(12) United States Patent
Ingbar et al.

(10) Patent No.: US 11,458,094 B2
(45) Date of Patent: Oct. 4, 2022

(54) COMPOSITIONS AND METHODS FOR TREATING PULMONARY EDEMA OR LUNG INFLAMMATION

(71) Applicant: REGENTS OF THE UNIVERSITY OF MINNESOTA, Minneapolis, MN (US)

(72) Inventors: David H. Ingbar, Minneapolis, MN (US); Timothy P. Rich, Duluth, MN (US); Robert J. Schumacher, Edina, MN (US); Jianxun Lei, New Brighton, MN (US); Maneesh Bhargava, Mendota Heights, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 0 days.

(21) Appl. No.: 16/965,095

(22) PCT Filed: Jan. 31, 2019

(86) PCT No.: PCT/US2019/016068
§ 371 (c)(1),
(2) Date: Jul. 27, 2020

(87) PCT Pub. No.: WO2019/152659
PCT Pub. Date: Aug. 8, 2019

(65) Prior Publication Data
US 2021/0113462 A1 Apr. 22, 2021

Related U.S. Application Data

(60) Provisional application No. 62/624,631, filed on Jan. 31, 2018.

(51) Int. Cl.
*A61K 9/00* (2006.01)
*A61K 31/198* (2006.01)
*A61P 11/00* (2006.01)

(52) U.S. Cl.
CPC .......... *A61K 9/0078* (2013.01); *A61K 31/198* (2013.01); *A61P 11/00* (2018.01)

(58) Field of Classification Search
CPC ..... A61K 9/0078; A61K 31/198; A61K 11/00
See application file for complete search history.

(56) References Cited

U.S. PATENT DOCUMENTS

| | | | |
|---|---|---|---|
| 9,913,819 B2 | 3/2018 | Kaminski et al. | |
| 2005/0281772 A1 | 12/2005 | Bromley et al. | |
| 2009/0148433 A1 | 6/2009 | Naidu et al. | |
| 2014/0199376 A1* | 7/2014 | Mousa | A61K 31/192 424/450 |
| 2015/0105519 A1* | 4/2015 | Chong | C07C 53/18 525/50 |
| 2016/0199309 A1 | 7/2016 | Mousa et al. | |
| 2017/0105956 A1* | 4/2017 | Kaminski | A61K 9/0075 |
| 2018/0030540 A1 | 2/2018 | Davicioni et al. | |

FOREIGN PATENT DOCUMENTS

| | | |
|---|---|---|
| WO | 2015/191841 | 12/2015 |
| WO | 2019/152659 | 8/2019 |
| WO | 2019/178023 | 9/2019 |

OTHER PUBLICATIONS

Bhargava et al, Triiodo-L-thyronine rapidly stimulates alveolar fluid clearance in normal and hyperoxia-injured lungs, American Journal of Respiratory and Critical Care Medicine, Vo. 178, 2008 (Year: 2008).*
MedBroadcast, Pulmonary fibrosis—Causes, Symptoms, Treatment, Diagnosis, MedBroadcast.com, obtained Aug. 10, 2021 (Year: 2021).*
Colombia University, Surgical lung and chest care, Interstitial lung disease and pulmonary fibrosis, obtained online on Jan. 4, 2022 (Year: 2022).*
Nafae et al., Thyroid function in respiratory failure patients. Egyptian J Chest Dis Tuberculosis, 63: 513-521 (2014).
Gore et al., Triiodothyronine (T3) Administration in Patients with Sepsis Induced Euthyroid Sick Syndrome: Hemodynamic and Metabolic Effects. Sepsis 2, 163-169 (1998).
Rich et al., D3 expression and activation are increased in ARDS with decreased tissue T3 in human lungs. American Journal of Respiratory and Critical Care Medicine, 181: A2716 (2010).
Loer et al., How much oxygen does the human lung consume? Anesthesiology 86, 532-537 (1997).
International Search Report and Written Opinion dated Apr. 15, 2019 for PCT/US2019/016068, filed Jan. 31, 2019. 8 pages.
International Preliminary Report on Patentability dated Aug. 4, 2020 for PCT/US2019/016068, filed Jan. 31, 2019. 6 pages.
Ingbar, David H. "Ion Transport in Resolution of Oxidant Induced Alveolar Edema," Grant Abstract, Grant No. HL050152 [online]. National Institutes of Health, project dates Approx. 1996-2003 [retrieved on Oct. 5, 2021] Retrieved from the Internet: reporter.nih.gov/search/4SpzSwpmgEC-bvYd9pzZcg/project-details/6839071; 4 pgs.
European Extended Search Report dated Oct. 8, 2021 for EP Application No. 19748160.9. 17 pages.
Sex Differences in Physiology: 2016, Elsevier Science. 1 page.
Anonymous: "Cell Culture Technology for Pharmaceutical and Cell-Based Therapies", 2005, Taylor & Francis (1 pg).
Anonymous: "Practical Pharmaceutics: An International Guideline for the Preparation, Care and Use of Medicinal Products", Aug. 24, 2015 (Aug. 24, 2015), Springer International Publishing.

(Continued)

*Primary Examiner* — Mina Haghighatian
(74) *Attorney, Agent, or Firm* — Mueting Raasch Group

(57) ABSTRACT

A pharmaceutical composition for administering directly to the pulmonary tract of a subject includes a salt of triiodothyronine and a pharmaceutically acceptable buffer, adjusted to pH of 5.5-8.5. The composition can be administered prophylactically or therapeutically to a subject to treat lung inflammation or pulmonary edema.

19 Claims, 14 Drawing Sheets

(56) References Cited

OTHER PUBLICATIONS

International Search Report and Written Opinion dated Jun. 8, 2021 for PCT/US2021/024345, filed Mar. 26, 2021. 9 pages.
Yu et al., Thyroid hormone inhibits lung fibrosis in mice by improving epithelial mitochondrial function. Nat Med 24, 39-49 (2018).
Woeber et al., The peripheral metabolism of triiodothyronine in normal subjects and in patients with hyperthyroidism. J Clin Invest 49, 643-649 (1970).
Woeber et al., The effects of an acute load of thyroxine on the transport and peripheral metabolism of triiodothyronine in man. J Clin Invest 49, 650-654 (1970).
Woeber, Levothyroxine therapy and serum free thyroxine and free triiodothyronine concentrations. J Endocrinol Invest 25, 106-109 (2002).
Wartofsky et al., Alterations in thyroid function in patients with systemic illness: the "euthyroid sick syndrome". Endocr Rev 3, 164-217 (1982).
Ware et al., Alveolar fluid clearance is impaired in the majority of patients with acute lung injury and the acute respiratory distress syndrome. Am J Respir Crit Care Med 163, 1376-1383 (2001).
Van Den Berghe, Endocrine changes in critically ill patients. Growth Horm IGF Res 9 Suppl A, 77-81 (1999).
Tierney, Lung metabolism and biochemistry. Annu Rev Physiol 36, 209-231 (1974).
Surks et al., Determination of iodothyronine absorption and conversion of L-thyroxine (T 4 ) to L-triiodothyronine (T 3 ) using turnover rate techniques. J Clin Invest 52, 805-811 (1973).
Simonides et al., Hypoxia-inducible factor induces local thyroid hormone inactivation during hypoxic-ischemic Iisease in rats. J Clin Invest 118, 975-983 (2008).
Silva et al., Pulmonary arterial hypertension and thyroid disease. J Bras Pneumol 35, 179-185 (2009).
Shao et al., Thyroid hormone stimulates Na, K-ATPase gene expression in the hemodynamically unloaded heterotopically transplanted rat heart. Thyroid 10, 753-759 (2000).
Sakka et al., Prognostic value of extravascular lung water in critically ill patients. Chest 122, 2080-2086 (2002).
Safer et al., A thyroid hormone deiodinase inhibitor can decrease cutaneous cell proliferation in vitro. Thyroid 19, 181-185 (2009).
Sabatino et al., Is the low tri-iodothyronine state a crucial factor in determining the outcome of coronary artery bypass patients? Evidence from a clinical pilot study. J Endocrinol 175, 577-586 (2002).
Richard et al., Ontogeny of iodothyronine deiodinases in human liver. J Clin Endocrinol Metab 83, 2868-2874 (1998).
Plikat et al., Frequency and outcome of patients with nonthyroidal illness syndrome in a medical intensive care unit. Metabolism 56, 239-244 (2007).
Pingitore et al., Acute effects of triiodothyronine (T3) replacement therapy in patients with chronic heart failure and low-T3 syndrome: a randomized, placebo-controlled study. J Clin Endocrinol Metab 93, 1351-1358 (2008).
Phua et al., Has mortality from acute respiratory distress syndrome decreased over time?: A systematic review. Am J Respir Crit Care Med 179, 220-227 (2009).
Phakdeekitcharoen et al., Thyroid hormone increases mRNA and protein expression of Na+-K+-ATPase alpha2 and beta1 subunits in human skeletal muscles. J Clin Endocrinol Metab 92, 353-358 (2007).
Perkins et al., The beta-agonist lung injury trial (BALTI): a randomized placebo-controlled clinical trial. Am J Respir Crit Care Med 173, 281-287 (2006).
Pace et al., The effects of hyperoxia exposure on lung function and pulmonary surfactant in a rat model of acute lung injury. Exp Lung Res 35, 380-398 (2009).
Oren-Grinberg, The PiCCO Monitor. Int Anesthesiol Clin 48, 57-85 (2010).
Olivares et al., Thyroid function disturbance and type 3 iodothyronine deiodinase induction after myocardial infarction in rats a time course study. Endocrinology 148, 4786-4792 (2007).
O'Grady et al., Chloride and potassium channel function in alveolar epithelial cells. Am J Physiol Lung Cell Mol Physiol 284, L689-700 (2003).
Norlin et al., Alveolar liquid clearance in the anesthetized ventilated guinea pig. Am J Physiol 274, L235-243 (1998).
Nauman et al., Total and free triiodothyronine in human serum. J Clin Invest 46,1346-1355 (1967).
Mullis-Jansson et al., A randomized double-blind study of the effect of triiodothyronine on cardiac function and morbidity after coronary bypass surgery. J Thorac Cardiovasc Surg 117, 1128-1134 (1999).
Morty et al., Alveolar fluid clearance in acute lung injury: what have we learned from animal models and clinical studies? Intensive Care Med 33, 1229-1240 (2007).
Morreale De Escobar et al., Effects of maternal hypothyroidism on the weight and thyroid hormone content of rat embryonic tissues, before and after onset of fetal thyroid function. Endocrinology 117, 1890-1900 (1985).
McIver et al., Euthyroid sick syndrome: an overview. Thyroid 7, 125-132 (1997).
Matthay et al., Intact epithelial barrier function is critical for the resolution of alveolar edema in humans. Am Rev Respir Dis 142, 1250-1257 (1990).
Matthay et al., Differential liquid and protein clearance from the alveoli of anesthetized sheep. J Appl Physiol Respir Environ Exerc Physiol 53, 96-104 (1982).
Matthay et al., Lung epithelial fluid transport and the resolution of pulmonary edema. Physiol Rev 82, 569-600 (2002).
Matthay et al., Invited review: Active fluid clearance from the distal air spaces of the lung. J Appl Physiol (1985) 93, 1533-1541 (2002).
Marvisi et al., Hyperthyroidism and pulmonary hypertension. Respir Med 96, 215-220 (2002).
Marks, Nonthyroidal illness syndrome in children. Endocrine 36, 355-367 (2009).
Lei et al., 3,3',5-Triiodo-L-thyronine up-regulation of Na,K-ATPase activity and cell surface expression in alveolar epithelial cells is Src kinase- and phosphoinositide 3-kinase-dependent. J Biol Chem 279, 47589-47600 (2004).
Lei et al., T3 increases Na-K-ATPase activity via a MAPK/ERK1/2-dependent pathway in rat adult alveolar epithelial cells. Am J Physiol Lung Cell Mol Physiol 294, L749-754 (2008).
Lei et al., Src kinase integrates PI3K/Akt and MAPK/ERK1/2 pathways in T3-induced Na-K-ATPase activity in adult rat alveolar cells. Am J Physiol Lung Cell Mol Physiol 301, L765-771 (2011).
Klemperer et al., Thyroid hormone treatment after coronary-artery bypass surgery. N Engl J Med 333,1522-1527 (1995).
Kaptein et al., rT3 metabolism in patients with nephrotic syndrome and normal GFR compared with normal subjects. Am J Physiol 260, E641-650 (1991).
Jonklaas et al., Single-dose T3 administration: kinetics and effects on biochemical and physiological parameters. Ther Drug Monit 37, 110-118 (2015).
Jobe, Hypocarbia and bronchopulmonary dysplasia. Arch Pediatr Adolesc Med 149, 615-616 (1995).
Jiang et al., Adrenergic regulation of ion transport across adult alveolar epithelial cells: effects on Cl-channel activation and transport function in cultures with an apical air interface. J Membr Biol 181, 195-204 (2001).
Jiang et al., Selectivity properties of a Na-dependent amino acid cotransport system in adult alveolar epithelial cells. Am J Physiol Lung Cell Mol Physiol 279, L911-915 (2000).
Jayr et al., Alveolar liquid and protein clearance in anesthetized ventilated rats. J Appl Physiol (1985) 76, 2636-2642 (1994).
Jassam et al., Consumptive hypothyroidism: a case report and review of the literature. Ann Clin Biochem 48, 186-189 (2011).
Ingbar, Pulmonary edema clearance: juicing up the sodium pump. Am J Respir Crit Care Med 171, 201-202 (2005).
Huppert et al., Alveolar Fluid Clearance in Pathologically Relevant Conditions: In Vitro and In Vivo Models of Acute Respiratory Distress Syndrome. Front Immunol 8, 371 (2017).
Huang et al., Severe hypothyroidism caused by type 3 iodothyronine deiodinase in infantile hemangiomas. N Engl J Med 343, 185-189 (2000).

(56) References Cited

OTHER PUBLICATIONS

Huang et al., Reawakened interest in type III iodothyronine deiodinase in critical illness and injury. Nat Clin Pract Endocrinol Metab 4, 148-155 (2008).
Hitchcock, Hormones and the lung. I. Thyroid hormones and glucocorticoids in lung development. Anat Rec 194, 15-39 (1979).
Heltianu et al., Evidence for thyroxine transport by the lung and heart capillary endothelium. Microvasc Res 37, 188-203 (1989).
Hamilton et al., Safety and hemodynamic effects of intravenous triiodothyronine in advanced congestive heart failure. Am J Cardiol 81, 443-447 (1998).
Forrest et al., Functions of thyroid hormone receptors in mice. Thyroid 10, 41-52 (2000).
Folkesson et al., Dexamethasone and thyroid hormone pretreatment upregulate alveolar epithelial fluid clearance ir adult rats. J Appl Physiol (1985) 88, 416-424 (2000).
Effros et al., New evidence for active sodium transport from fluid-filled rat lungs. J Appl Physiol (1985) 66, 906-919 (1989).
Craig et al., Extravascular lung water indexed to predicted body weight is a novel predictor of intensive care unit mortality in patients with acute lung injury. Crit Care Med 38, 114-120 (2010).
Chopra et al., An inhibitor of the binding of thyroid hormones to serum proteins is present in extrathyroidal tissues. Science 215, 407-409 (1982).
Bosma et al., Pharmacotherapy for prevention and treatment of acute respiratory distress syndrome: current and experimental approaches. Drugs 70, 1255-1282 (2010).
Boelen et al., Type 3 deiodinase is highly expressed in infiltrating neutrophilic granulocytes in response to acute bacterial infection. Thyroid 18, 1095-1103 (2008).
Bianco et al., Biochemistry, cellular and molecular biology, and physiological roles of the iodothyronine selenodeiodinases. Endocr Rev 23, 38-89 (2002).
Bhargava et al., Triiodo-L-thyronine rapidly stimulates alveolar fluid clearance in normal and hyperoxia-injured lungs. Am J Respir Crit Care Med 178, 506-512 (2008).
Bhargava et al., Thyroid hormone rapidly stimulates alveolar Na,K-ATPase by activation of phosphatidylinositol 3-kinase. CurrOpin Endocrinol Diabetes Obes 14, 416-420 (2007).
Berkowitz et al., Accurate characterization of extravascular lung water in acute respiratory distress syndrome. Crit Care Med 36, 1803-1809 (2008).
Bennett-Guerrero et al., Cardiovascular effects of intravenous triiodothyronine in patients undergoing coronary artery bypass graft surgery. A randomized, double-blind, placebo-controlled trial. Duke T3 study group. JAMA 275, 687-692 (1996).
Bello et al., Nonthyroidal illness syndrome and prolonged mechanical ventilation in patients admitted to the ICU. Chest 135, 1448-1454 (2009).
Bastian et al., Perinatal iron and copper deficiencies alter neonatal rat circulating and brain thyroid hormone concentrations. Endocrinology 151, 4055-4065 (2010).
Basset et al., Significance of active ion transport in transalveolar water absorption: a study on isolated rat lung. J Physiol 384, 311-324 (1987).
Barker et al., The effect of thyroidectomy in the fetal sheep on lung liquid reabsorption induced by adrenaline or cyclic AMP. J Physiol 407, 373-383 (1988).
Armigliato et al., Hyperthyroidism as a cause of pulmonary arterial hypertension: a prospective study. Angiology 57, 600-606 (2006).
Abraham et al., HMG-1 as a mediator of acute lung inflammation. J Immunol 165, 2950-2954 (2000).
Flory et al., "Development of Thyroid Hormone as a Treatment Therapy for Acute Respiratory Distress Syndrome" Poster presented at The University of Minnesota's Rare Diseases Conference, Minneapolis, MN; Feb. 23, 2018.
Lei et al., "3,5,3'-L-Thyroxine Decreases Hyperoxia-Induced Lung Injury in Rats" Poster Abstract. Wednesday, May 20; San Diego Convention Center. Am J Respir Crit Care Med 179; 2009:A5644.
Lei et al., Thyroid hormone stimulates Na-K-ATPase activity and its plasma membrane insertion in rat alveolar epithelial cells. Am J Physiol Lung Cell Mol Physiol 285, L762-772 (2003).
Lei et al., Cell-specific signal transduction pathways regulating Na+-K+-ATPase. Focus on "short-term effects of thyroid hormones on the Na+-K+-ATPase activity of chick embryo hepatocytes during development: focus on signal transduction". Am J Physiol Cell Physiol 296, C1-3 (2009).
Lei et al., Developmental acquisition of T3-sensitive Na-K-ATPase stimulation by rat alveolar epithelial cells. Am J Physiol Lung Cell Mol Physiol 292, L6-14 (2007).
Bhargava et al., Nongenomic actions of L-thyroxine and 3,5,3'-triiodo-L-thyronine. Focus on "L-Thyroxine vs. 3,5,3'-triiodo-L-thyronine and cell proliferation: activation of mitogen-activated protein kinase and phosphatidylinositol 3-kinase". Am J Physiol Cell Physiol 296, C977-979 (2009).
Lado-Abeal, Thyroid hormones are needed to sustain "inappropriately" normal TSH during non-thyroidal illness syndrome: a clinical observation in severely ill patients with primary hypothyroidism. Neuro Endocrinol Lett 36, 41-47 (2015).
Bringardner et al., The Role of Inflammation in the Pathogenesis of Idiopathic Pulmonary Fibrosis. Antioxid Redox Signal, 10(2): 287-301 (Feb. 2008).
Crapo, Morphologic Changes in Pulmonary Oxygen Toxicity. Ann Rev Physiol 48: 721-31 (1986).
Ismail-Beigi, Thyroid hormone regulation of Na,K-ATPase expression. Trends Endocrinol Metab 4, 152-155 (1993).

\* cited by examiner

A

B

A

B

C

Room Air Control 60 hr

Hyperoxia 60 hr

Hyperoxia 60 hr

Control

COMPOSITIONS AND METHODS FOR TREATING PULMONARY EDEMA OR LUNG INFLAMMATION

CROSS-REFERENCE TO RELATED APPLICATION

This application is the § 371 U.S. National Stage of International Application No. PCT/US2019/016068, filed Jan. 31, 2019, which claims priority to U.S. Provisional Patent Application No. 62/624,631 filed Jan. 31, 2018, each of which is incorporated herein by reference in its entirety.

GOVERNMENT FUNDING

This invention was made with government supportt under HL050152 awarded by the National Institutes of Health. The government has certain rights in the invention.

SUMMARY

This disclosure describes, in one aspect, a pharmaceutical composition for administering directly to the pulmonary tract (e.g., nasosinus, intratracheal, intrabronchial, or alveolar airspace) of a subject. Generally, the composition includes a salt of triiodothyronine and a pharmaceutically acceptable buffer, adjusted to a pH of 5.5-8.5.

In some embodiments, the salt of triiodothyronine is provided in an amount of at least 5 μg per 10 ml.

In some embodiments, the composition is aerosolized. In other embodiments, the composition is nebulized.

In another aspect, this disclosure describes a method for treating a subject having, or at risk of having inflammation of lung tissues. Generally, the method includes administering to the subject an amount of triiodothyronine effective to ameliorate lung inflammation, wherein the triiodothyronine is administered directly to the pulmonary tract.

In some embodiments of either method, the triiodothyronine is administered by instillation. In other embodiments of either method, the triiodothyronine is administered by inhalation of an aerosolized formulation. In still other embodiments of either method, the triiodothyronine is administered by inhalation of a nebulized formulation.

In some embodiments of either method, the triiodothyronine is administered to a lung-delivered drug dose range of 10 ng to 5 mg.

In some embodiments of either method, the triiodothyronine is administered prior to the subject manifesting any symptom or clinical sign of lung inflammation or pulmonary edema.

In some embodiments of either method, the triiodothyronine is administered after the subject manifests a symptom or clinical sign of lung inflammation or pulmonary edema.

In some embodiments of either method, the lung inflammation or pulmonary edema is a clinical sign of acute respiratory distress syndrome (ARDS).

In some embodiments of either method, the lung inflammation or pulmonary edema is a symptom or clinical sign of premature birth, chest trauma, congestive heart failure, lung transplant, lung cancer radiotherapy, lung cancer chemotherapy, smoking, exposure to a pollutant, hypersensitivity pneumonitis, a reactive/obstructive lung disease, aspiration chemical pneumonitis/pneumonia, pneumonia, an infection of the nasosinus, intratracheal, intrabronchial or alveolar airspace, a connective tissue disease, Wegener's granulomatosis, Good pasture disease, acute eosinophilic pneumonia, chronic eosinophilic pneumonia, medication-related lung injury, cryptogenic organizing pneumonia, Churg-Strauss syndrome, congenital lung disease, or structural lung disease.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The patent or application file contains at least one drawing or photograph executed in color. Copies of this patent or patent application publication with color drawings or photographs will be provided by the Office upon request and payment of the necessary fee.

DETAILED DESCRIPTION OF ILLUSTRATIVE EMBODIMENTS

Figure 1:
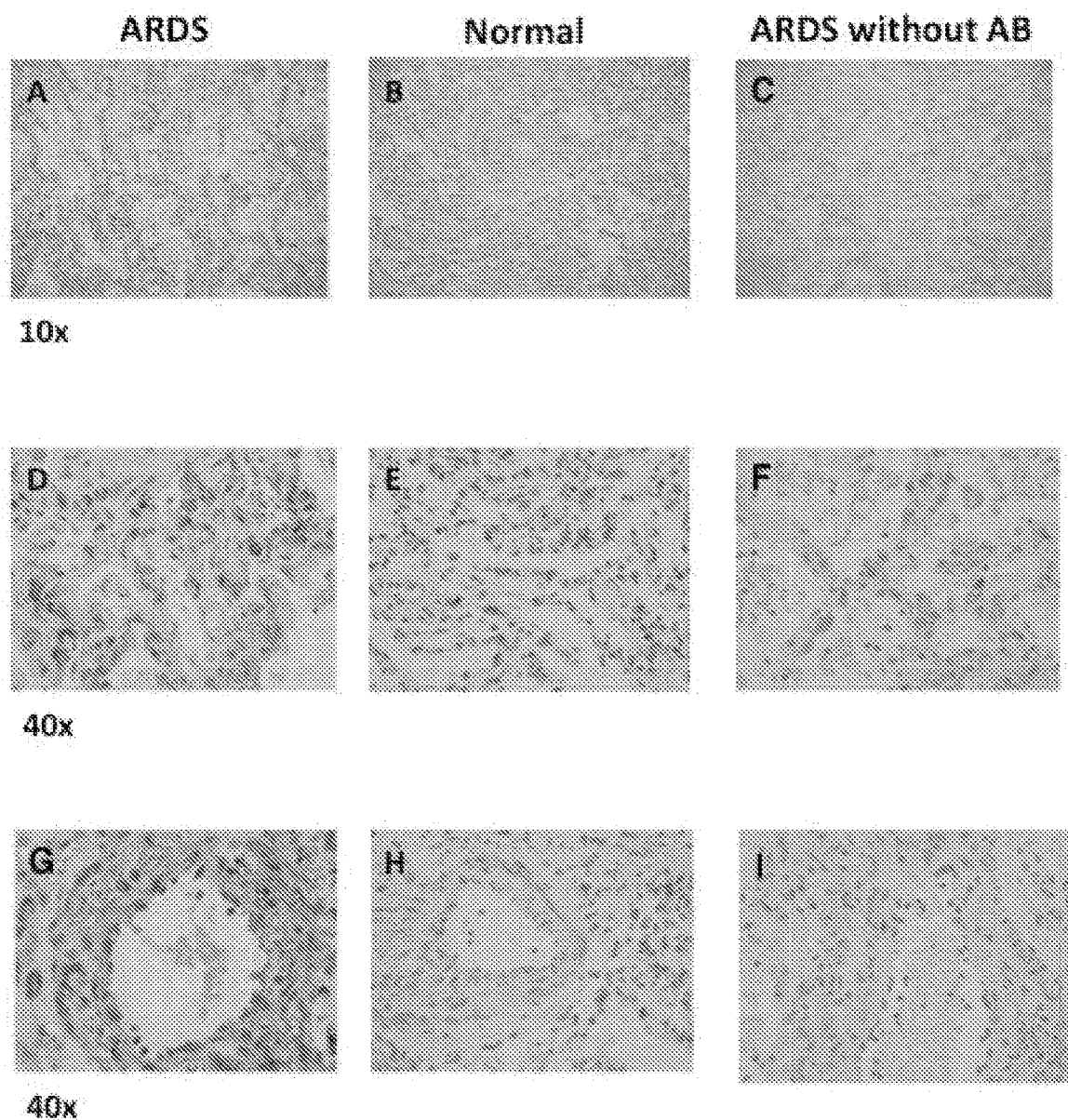
FIG. 1. Immunohistochemical localization of the enzyme deiodinase-3 (D3) in lung tissue from acute respiratory distress syndrome (ARDS) patients and normal human. (A) ARDS tissue samples showed characteristic diffuse alveolar damage and proteinaceous alveolar filling in the air spaces with diffusely positive D3 staining in multiple cell types. (D) ARDS tissue samples showed hyaline membrane formation with D3-positive staining of type II alveolar pneumocytes. (G) ARDS tissue samples showed proliferation and inflammatory cells in the interstitium with D3-positive staining of spindle-shaped cells and capillary endothelium. (B, E, H) Control tissue samples from normal human lung demonstrated normal histologic architecture of the alveoli and interstitium without significant D3 staining. (C, F, I) ARDS samples processed with normal mouse serum, rather than primary antibody (as a specificity control), also demonstrated no significant D3 staining.

This disclosure describes compositions that include triiodothyronine (T3) is effective for treating pulmonary edema and/or lung inflammation such as, for example, processes that occur in acute respiratory distress syndrome (ARDS). The T3 compositions are formulated to be administered directly into the lung, whether in a liquid form or as an aerosol. This disclosure further describes methods of treating lung inflammation by administering a formulation of T3 directly to the nasosinus, intratracheal, intrabronchial, or alveolar space.

The lung is a target tissue of thyroid hormone (TH). Thyroid hormone affects lung development, lung function, and repair of injury to lung tissues. In rodents, hypothyroidism impairs clearance of airspace fluid during lung development, while systemic T3 augments alveolar fluid clearance in adult rat lungs. T3 stimulation of alveolar fluid clearance occurs locally and rapidly in the lung. Further, mouse models with knockout of either the thyroid hormone receptor (TR) alpha or beta genes have altered lung development, and response to stress and injury. In sheep models, preterm lambs showed significant improvement in perinatal lung function when thyroxine was added to betamethasone injections.

Clinically, thyroid disorders are associated with diverse pulmonary symptoms. Both hypothyroidism and hyperthyroidism may cause respiratory muscle weakness and/or decreased pulmonary function. Hypothyroidism reduces respiratory drive and also can cause obstructive sleep apnea or pleural effusions. Conversely, hyperthyroidism increases respiratory drive and can cause dyspnea on exertion. Either hypothyroidism or hyperthyroidism, can be associated with idiopathic primary pulmonary arterial hypertension (IPPAH). Further, treating the underlying thyroid disorder may reverse pulmonary hypertension, although the exact mechanism involved in the pathogenesis is not established.

At the cellular level, thyroid hormone status affects alveolar number, the number and size of alveolar type II pneumocyte cells, and their surfactant production. T3 increases alveolar fluid clearance (AFC) in alveolar epithelial cells through augmented Na,K-ATPase activity. Active sodium resorption is involved in clearing pulmonary (alveolar) edema in lungs at birth, in acute lung injury (ALI), in acute respiratory distress syndrome (ARDS), and in cardiogenic edema, such as congestive heart failure. Conversely, reducing T3 levels in the lung can exacerbate alveolar edema.

This disclosure describes methods that involve administering T3 directly to the nasosinus, intratracheal, intrabronchial, or alveolar airspace by, for example, spray, inhalation, nebulization, or instillation. While described herein in the context of an exemplary embodiment in which alveolar edema and/or lung inflammation are associated with acute respiratory distress syndrome (ARDS), the compositions and methods described herein can be used to treat alveolar edema and/or inflammation of lung tissue regardless of the underlying cause of the inflammation. Exemplary other causes of lung inflammation or alveolar edema that are treatable using the compositions and methods described herein include, for example, premature birth, chest trauma, congestive heart failure, pre- and/or post-lung transplant, pre- and/or post-lung cancer radiotherapy or chemotherapy, pneumonia, sepsis, smoking (whether tobacco or THC), exposure to pollutants (whether environmental or occupational, e.g., asbestosis, silicosis, berylliosis, Coal Worker's, pneumoconiosis, gas exposure, thermal injury, or other pneumoconiosis), hypersensitivity pneumonitis, reactive or obstructive lung diseases (e.g., asthma, chronic bronchitis, reactive airway dysfunction syndrome, or other reactive airway diseases), aspiration chemical pneumonitis or pneumonia, pneumonia or an infection of nasosinus, intratracheal, intrabronchial or alveolar airspace (e.g., bacterial, viral, fungal), connective tissue diseases (e.g., rheumatoid arthritis, systemic lupus erythematosus, scleroderma, sarcoidosis, and other related diseases), Wegener's granulomatosis, Good pasture disease, acute or chronic eosinophilic pneumonia, medication-related lung injury (e.g., injury from use of amiodarone, bleomycin, busulfan, mitomycin C, methotrexate, apomorphine, nitrofurantoin, or other pneumotoxic drugs), cryptogenic organizing pneumonia, Churg-Strauss syndrome, or congenital or structural lung disease (e.g., cystic fibrosis, bronchiectasis.

Acute respiratory distress syndrome (ARDS) is characterized by hemorrhagic inflammatory pulmonary edema with decreased alveolar fluid clearance (AFC) and high mortality. Triiodothyronine (T3) acts on alveolar type II pneumocytes to augment their Na,K-ATPase activity, thereby promoting edema fluid clearance and augmenting oxygen diffusion into the capillaries. T3 is inactivated by enzyme iodothyronine deiodinase type-III (D3). Most patients with ARDS have reduced ability to clear alveolar edema fluid. Moreover, a slower rate of alveolar fluid clearance is associated with higher mortality and longer requirement for support with mechanical ventilation. Thus, improving alveolar fluid clearance can improve outcomes for patients with ARDS. This disclosure reports that D3 expression and activity are elevated in early ARDS human lung tissue. D3 induction in early ARDS is accompanied by local lung T3 inactivation, resulting in a decrease in lung T3 concentration in lung tissue. Given that T3 stimulates alveolar fluid clearance, D3-induced inactivation of lung T3 may impede alveolar fluid clearance in ARDS, contributing to the degree of alveolar flooding with fluid and the persistent hypoxemia.

ARDS lung tissue samples showed characteristic diffuse alveolar damage with proteinaceous alveolar filling within the air spaces, hyaline membrane formation and inflammatory cells in the interstitium (FIGS. 1A, 1D, 1G). Control tissue samples demonstrated normal histologic architecture of the alveoli and interstitium (FIGS. 1B, 1E, 1H). Immunohistochemical localization of D3 in ARDS tissue revealed high level D3 expression in alveolar type II pneumocytes (FIGS. 1A, 1D), spindle-shaped interstitial cells, and capillary endothelial cells (FIG. 1G). Normal control tissue demonstrated much less D3 antibody staining in all of these cell types (FIGS. 1B, 1E, 1H). As a specificity control, removal of primary antibody resulted in no significant D3 staining of any tissue sections (FIGS. 1C, 1F, 1I).

Figure 2:
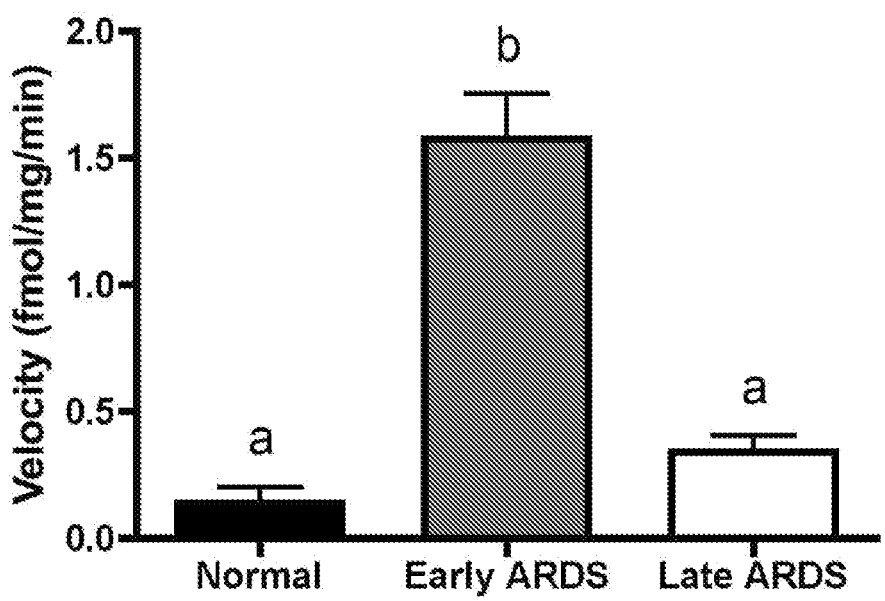
FIG. 2. Deiodinase-3 activity and T3 quantity in lung tissue of ARDS and normal human lungs. Lung D3 enzymatic activity is elevated in early ARDS lungs and lung T3 concentration is decreased in both early and late ARDS lungs. D3 activity (A) and total T3 concentrations (B) were measured in post-mortem human early ARDS (n=3), late ARDS (n=5) and normal control (n=4) lungs. Data are presented as mean±SEM. Groups not sharing a common superscript are significantly different by one-way ANOVA and Tukey's multiple comparison test ($P<0.05$).
Figure 2:
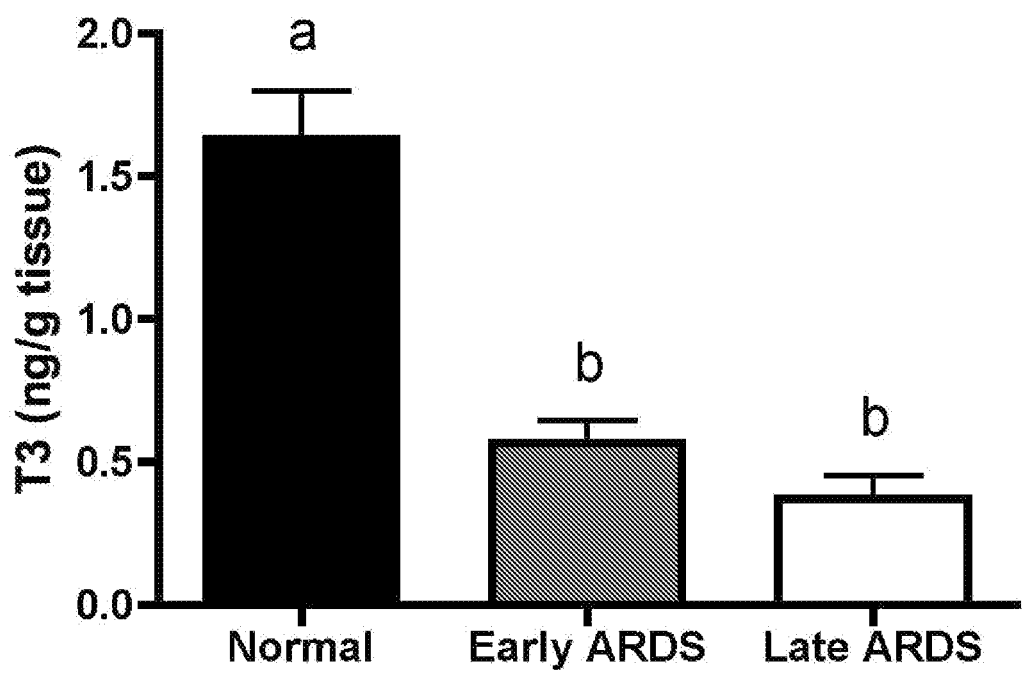
Figure 3:
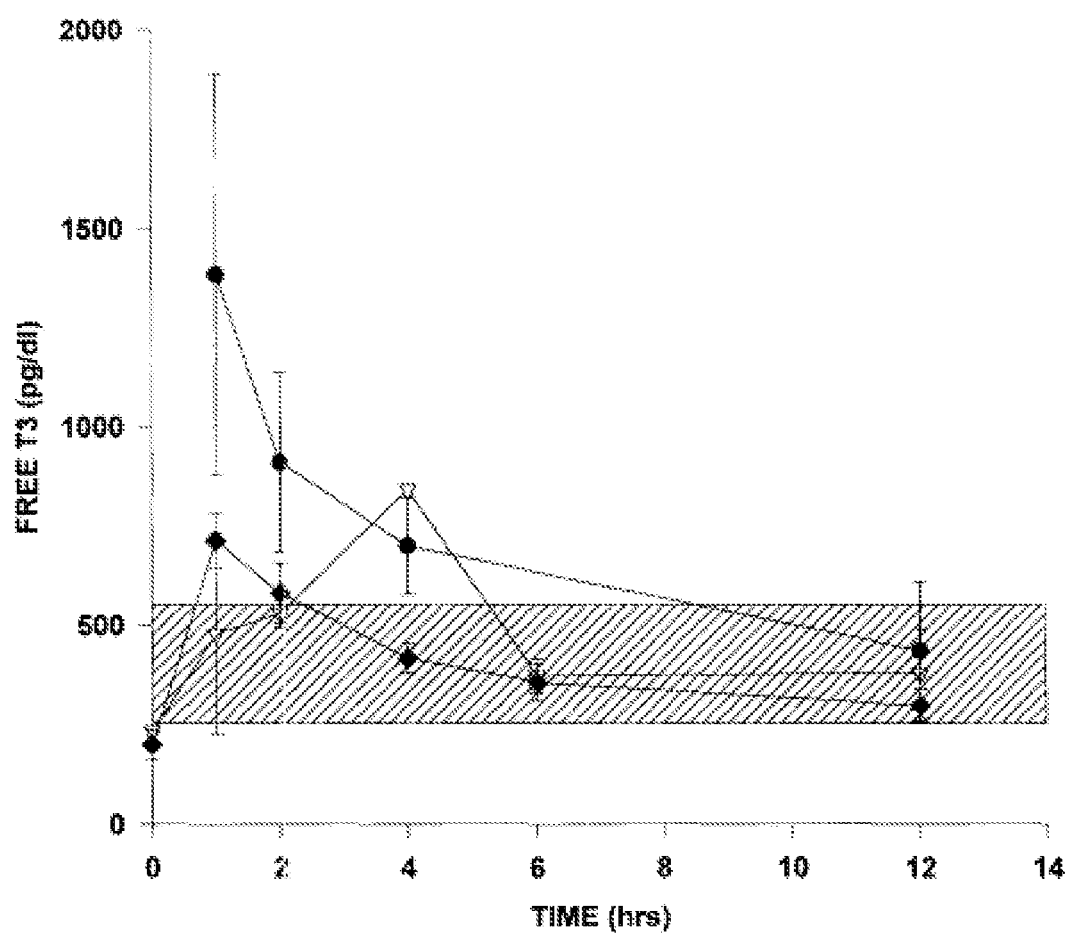
FIG. 3. Free T3 levels after single or dual T3 dosing protocols. Mean±SD free triiodothyronine (T3) levels by dosing groups for human patients receiving only bolus of triiodothyronine as follows: 0.05 μg/kg at 0 hours+0.1 μg/kg at three hours (open triangles), 0.2 μg/kg at 0 hours (filled circles), or 0.4 μg/kg at 0 hours (filled diamonds). The shaded box represents the normal range for serum free triiodothyronine levels.
Figure 4:
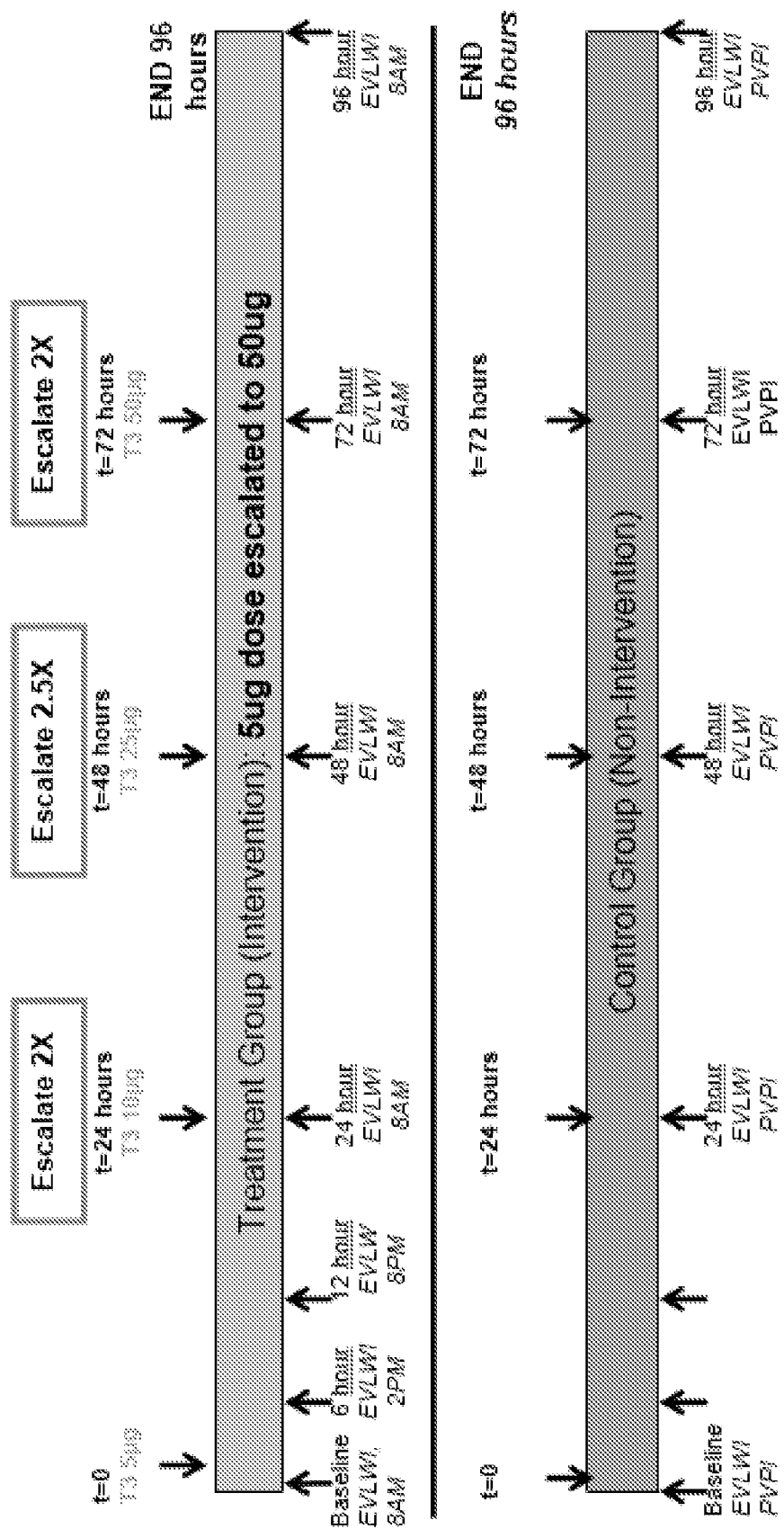
FIG. 4. Design of FDA-approved Phase I/II clinical human trial of T3 instillation for treating ARDS.

To determine whether the increase in D3 expression in ARDS lungs was associated with increased enzymatic activity, D3 enzyme activities were measured in early ARDS (n=3), late ARDS (n=5), and control (n=4) lung samples. Lung D3 enzyme activity was approximately 11.3 times higher in early ARDS versus normal control tissue (1.57 vs. 0.14±SEM fmol/mg/min, $p<0.0001$) (FIG. 2A). D3 activity was approximately 2.5 times higher in late ARDS vs control lungs (0.34 vs 0.14 fmol/mg/min, p=0.29, n.s.). Lung T3 levels were 65% and 77% lower in early and late ARDS, respectively, compared to control lung levels (FIG. 2B). Together, these data demonstrate that D3 expression and activity are markedly induced in the lungs of early ARDS patients and the increased D3 is associated with local reduction in total tissue T3. These data connect the role of T3 in promoting alveolar fluid clearance (AFC) in ARDS and the role of D3 causing T3 inactivation in hypoxic, inflammatory conditions.

In lung injury, the permeability of the alveolar epithelium and the capillary endothelium are increased, allowing ready transcapillary diffusion of proteins, solutes, and fluid into the interstitium and alveolar space. Resorption of interstitial edema and, particularly, alveolar edema fluid is crucial for efficient gas exchange in the alveoli. Alveolar fluid clearance is driven by active alveolar epithelial sodium resorption across the alveolar epithelial barrier through combined action of basolateral Na,K-ATPase pump and apical sodium transport proteins.

In both normal and in injured rat lungs, T3 instillation significantly increases alveolar fluid clearance. Local and/or systemic inflammation may initiate D3 induction in the ARDS lung. Acute bacterial infections and/or infarction/ischemia can trigger D3 expression. The ARDS in the patients of this study resulted from a variety of etiologies, including pneumonia (viral or bacterial), sepsis, trauma, and post-surgical lung injury, all with inflammation as the likely common pathway to D3 induction and subsequent T3 depletion. Decreased local T3 concentration in the ARDS lung impedes alveolar fluid clearance. The decreased alveolar fluid clearance impairs oxygen diffusion and exacerbates hypoxemia, a hallmark of ARDS. At baseline in normal circumstances, five percent of total-body oxygen uptake is consumed for the mechanics of respiration and lung function. In critical illness, such as respiratory failure, the metabolic requirements of the lung usually are significantly increased to maintain adequate oxygenation and ventilation. In ARDS, systemic and local inflammation likely augment systemic and local expression of D3, lowering T3 level and downregulating lung metabolism at a time when accelerated function may be desired. Because all other organs depend on the lung gas exchange for oxygen, and because T3 is involved in maintaining alveolar fluid clearance and diffusing capacity, T3 deficiency in the lung has a deleterious effect.

T3 instillation augments alveolar fluid clearance in normal and hyperoxia-injured lung tissue. Hyperoxia-induced lung injury (HALI) is a well-established animal model of acute lung injury. Hyperoxia-generated reactive oxygen species (ROS) lead to alveolar epithelial and endothelial cell death by apoptosis and necrosis, contributing to lung injury. The molecular basis of oxygen toxicity is mediated by free radical ROS (reactive oxygen species) derived directly from molecular oxygen and/or derived indirectly from interactions of molecular oxygen with other species. Oxidants therefore mediate the development of acute and chronic lung injuries. Thyroid hormone affects antioxidant defenses of both adult and developing rat brain and lung. This disclosure presents data evaluating the effects of systemic T3 supplementation on lung inflammation and injury in the HALI model.

Figure 13:
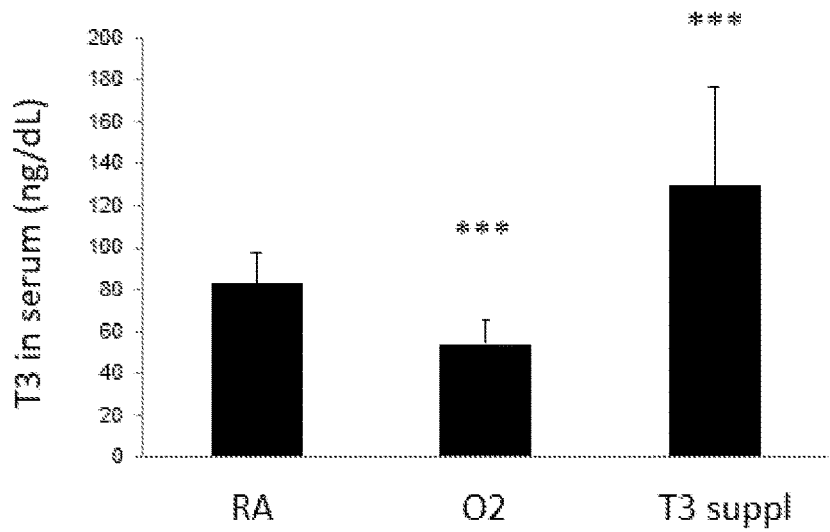
FIG. 13. Hyperoxia decreased serum total T3 concentration. Rats were exposed to ~95% of oxygen for 60 hours. T3 supplementation started after 24 hours of hyperoxia exposure. Data are presented as mean±standard deviation (SD) of independent experiments (8 rats for room air control, 10 rats for hyperoxia, six rats for T3 supplementation) ***, p<0.001. RA: room air control.

Hyperoxia decreased serum total T3 levels. Critical illness often causes the euthyroid sick syndrome or nonthyroidal illness, with decreases of serum total and free T3 concentrations. FIG. 13 shows data measuring the total serum T3 levels in rats exposed to 95% oxygen for 60 hours with or without intraperitoneal T3 supplementation (50 µg/kg bodyweight/24 hours). Hyperoxia significantly reduced the serum total T3 compared with normoxic room air (RA) rats (RA: 82.97±14.4399, hyperoxia: 53.9±11.2953, p=0.00043), and supplementation augmented serum total T3.

Figure 14:
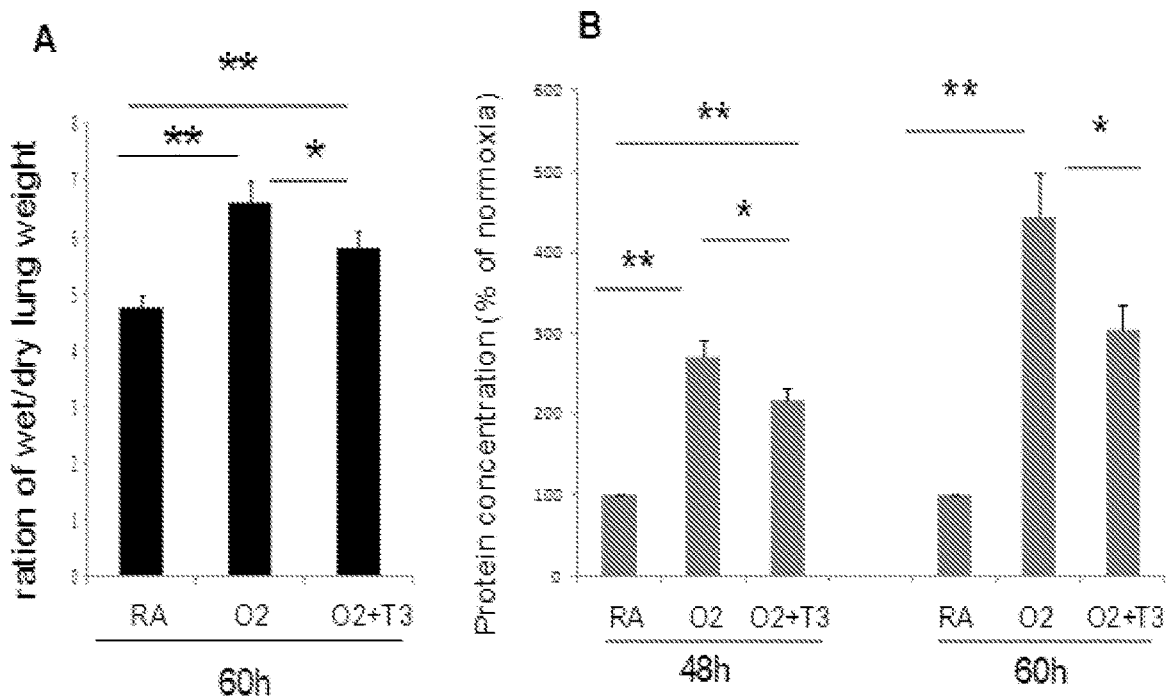
FIG. 14. Effects of T3 on hyperoxia-induced indicia. (A) T3 diminishes hyperoxia-induced increases of wet/dry lung weight ratio. (B) T3 diminishes hyperoxia-induced increases of bronchoalveolar lavage (BAL) fluid protein concentration. Data are presented as mean±SD of independent experiments (four rats from two experiments for 48-hour exposure; three rats from three experiments for 60-hour exposure). *, p<0.05; **, p<0.01. RA: room air control.

T3 decreased the hyperoxia-induced increases in lung edema and bronchoalveolar lavage fluid (BALF) protein concentration. Adult rats exposed to 95% oxygen for 60 hours have substantial lung injury as documented by increases in BALF protein concentration, permeability, and lung edema. Hyperoxia induces increased wet-to-dry lung weight ratios compared to normoxic rat lungs (6.49±0.27 vs. 5.3±0.16, respectively, p=0.004). FIG. 14A shows that 60 hours of hyperoxia again markedly increased the wet-to-dry lung weight ratio compared with room air ($O_2$ 6.61±0.60 vs. RA 4.82±0.14). Treatment with intraperitoneal T3 (12.5 µg/kg body weight injected each 12 hours) significantly decreased this hyperoxia-induced increase ($O_2$: 6.61±0.604; $O_2$ with T3: 5.82±0.197, p=0.0495 vs $O_2$ treatment) (FIG. 14A). Hyperoxia also increased markedly the BALF protein concentration at both the 48 hour and 60 hour time points, and T3 administration attenuated significantly the hyperoxic increases in the BALF protein concentration at both time points (FIG. 14B). Thus, T3 supplementation decreased the extent of pulmonary edema and the dysfunction of the alveolar epithelial barrier caused by hyperoxia.

Figure 15:
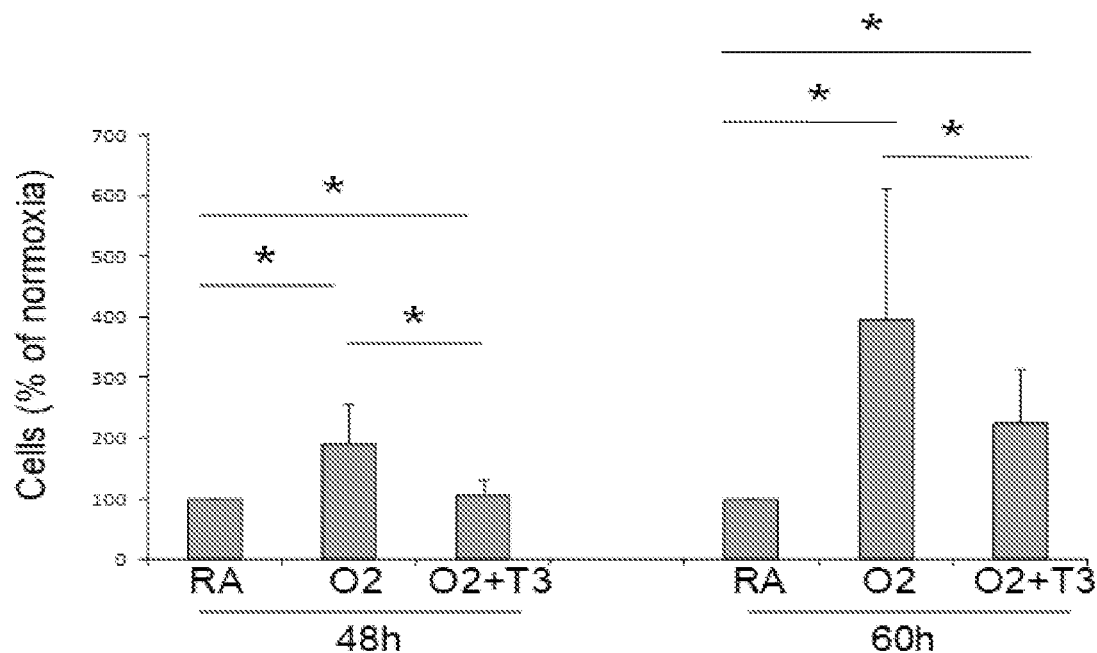
FIG. 15. T3 decreases hyperoxia-induced increase of BALF nucleated cells. Data are presented as mean±SD of independent experiments (four rats from two experiments for 48-hour exposure; four rats from three experiments for 60-hour exposure). *, p<0.05; **, p<0.01. RA: room air control.

T3 reduced the hyperoxic increases of BALF cellularity and lung tissue neutrophil accumulation. In adult rat lungs 95% oxygen exposure augmented the number of inflammatory cells in BALF. Indeed, 48 hours or 60 hours exposure to 95% oxygen markedly increased the number of bronchoalveolar lavage (BAL) cells compared to the control rats in the room air. Most of the BAL cells were mononuclear cells and macrophages, but differential cell counts were not performed. T3 administration during hyperoxia significantly reduced the BALF cell numbers at both time points compared with their hyperoxia alone counterparts (FIG. 15).

Figure 16:
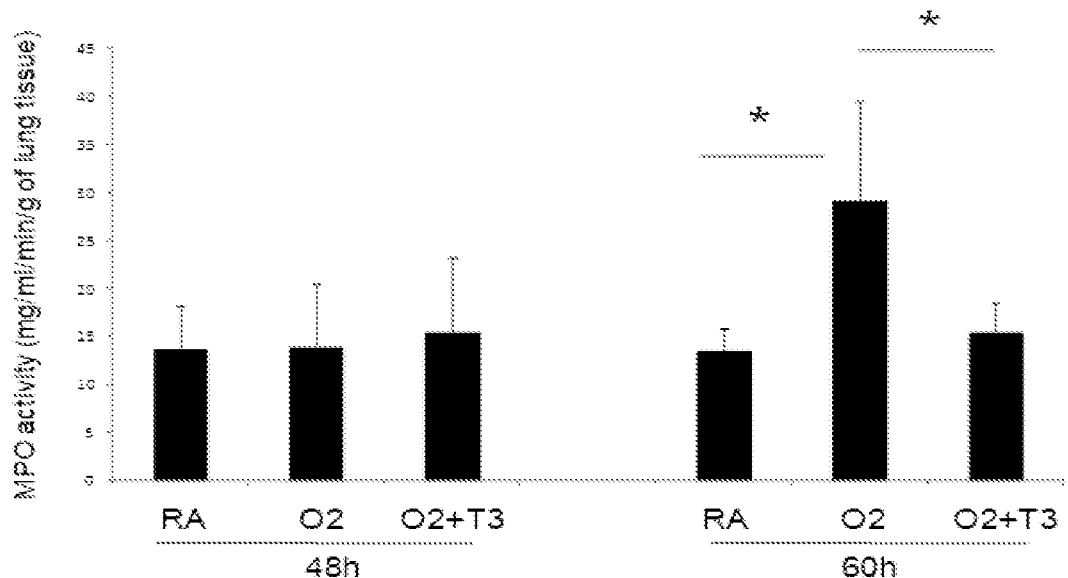
FIG. 16. T3 decreases hyperoxia-induced myeloperoxidase (MPO) activity in lung tissue. Data are presented as mean±SD. of independent experiments (four rats from two experiments for 48-hour exposure; four rats from three experiments for 60-hour exposure). *, p<0.05; **, p<0.01. RA: room air control.
Figure 17:
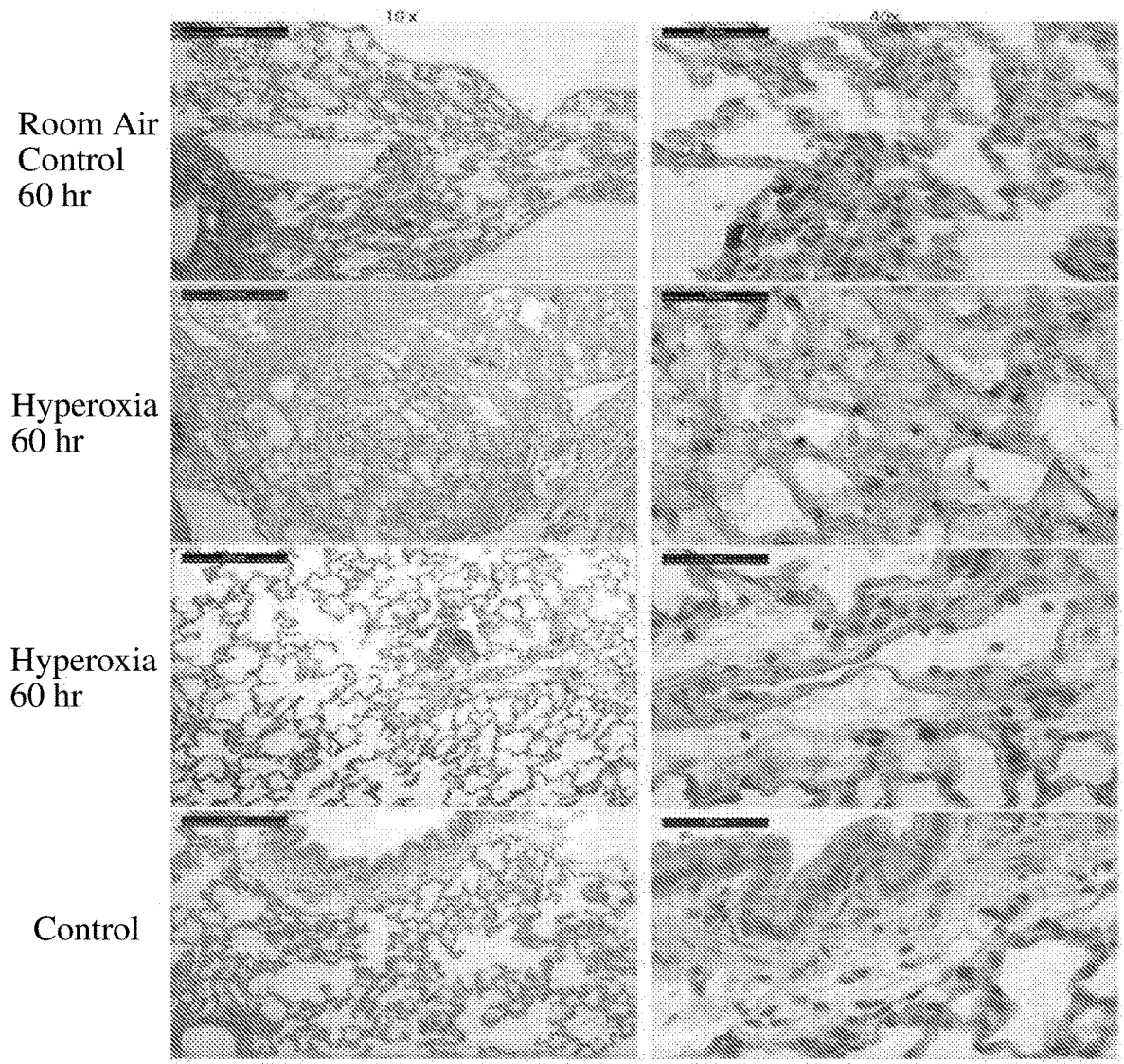
FIG. 17. T3 decreases lung neutrophils (MPO-positive cells) after hyperoxia. Lung tissues were obtained at 60 hours after hyperoxia exposure with/without T3 injections. Immunostaining was performed with primary: anti-MPO antibody. Black dots represent MPO-positive cells.

Neutrophil infiltration into the lung is a component of lung inflammation that often is a prelude to and component of lung injury. However, relatively few of the BALF cells after hyperoxia were neutrophils (data not shown). The effects of T3 on lung tissue neutrophils under hyperoxia were directly assessed in two ways: measurement of myeloperoxidase (MPO) activity in lung homogenates and immunostaining of the lungs for MPO. Although lung MPO activity was not altered by hyperoxia at 48 hours (FIG. 16, left panel), lung MPO activity was markedly increased at 60 hours of hyperoxia compared to room air controls (FIG. 16, right panel). T3 supplementation significantly reduced the hyperoxia-induced MPO activity (FIG. 16, right panel). Similarly, cytochemistry demonstrated that the T3-injected rats exposed to 95% oxygen for 60 hours displayed fewer MPO-positive cells in the lungs compared with hyperoxic lungs without T3 supplementation, confirming the MPO activity results (FIG. 17). Systemic T3 supplementation inhibited the hyperoxia-induced neutrophil accumulation within the lung tissue.

T3 reduced the hyperoxia-induced morphologic lung injury. Histopathological evaluation of lung sections also was performed to assess qualitatively whether T3 reduced hyperoxic lung injury. As expected, hyperoxia alone caused alveolar septal thickening, lung edema, and alveolar inflammatory cells (FIGS. 18A and 18B). In contrast, systemic T3 supplementation led to the persistence of virtually normal lung morphology (FIG. 18C). The striking difference in lung histology further demonstrated that T3 supplementation significantly attenuated hyperoxic lung injury.

Thus, this disclosure provides data showing that T3 administration concomitant with the hyperoxic exposure significantly decreased the severity of hyperoxia-induced rat lung injury, with reduced neutrophil accumulation in the lungs, diminished lung edema, and less breakdown of the alveolar epithelial permeability barrier. T3 supplementation significantly reduced, but did not completely eliminate the hyperoxic lung injury and inflammation. These results strongly suggest a protective anti-inflammatory effect of T3 against hyperoxic lung injury.

Figure 18:
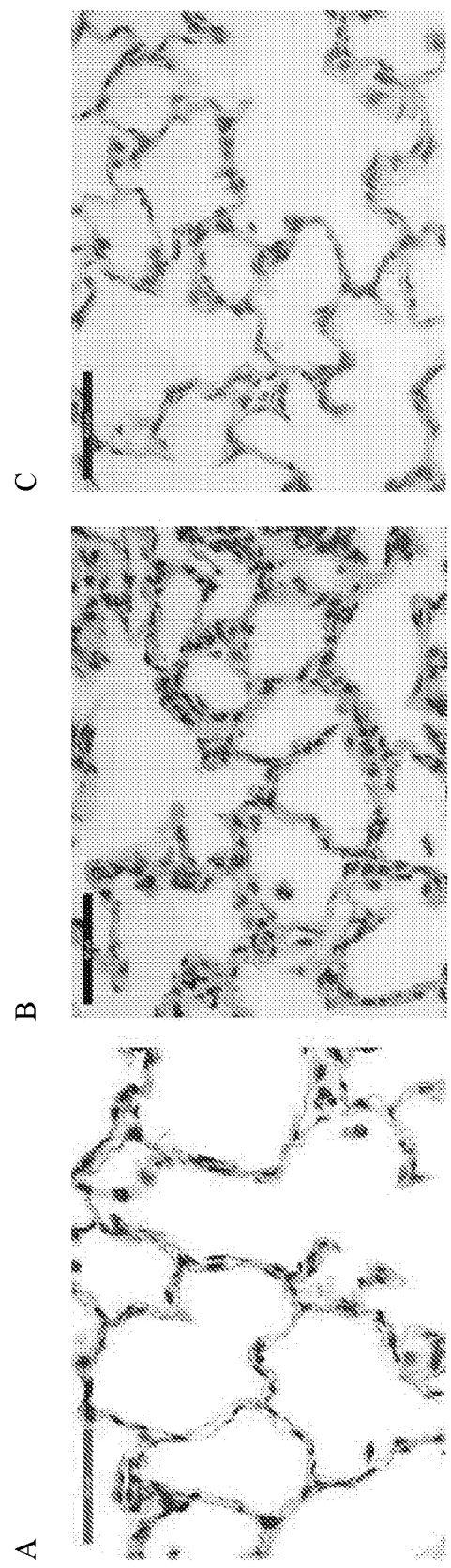
FIG. 18. T3 injection reduces morphologic hyperoxic lung injury. Rat lung tissues at 60 hours of hyperoxia exposure with/without T3 injections were stained with hematoxylin, and examined by light microscopy. (A) Control: room air; (B) Hyperoxia; (C) Hyperoxia+T3.

Hyperoxia exposure decreased the serum total T3 concentration (FIG. 13). Intraperitoneal injections of T3 restored the serum total T3 (FIG. 13) and significantly decreased the hyperoxia-mediated lung injury in adult rats, as measured by a reduction in the increases of: (1) the ratio of wet/dry lung weight at 60 hours (FIG. 14A); (2) the BAL:fluid total protein concentration at 48 hours or 60 hours after exposure (FIG. 14B); (3) the number of nucleated cells in BAL fluid at 48 hours or 60 hours (FIG. 15); (4) neutrophil accumulation in lung tissue at 60 hours (FIG. 16 and FIGS. 17); and (5) the histopathologic diffuse alveolar wall injury and infiltration with inflammatory cells in rat lungs at 60 hours (FIG. 18). These results demonstrate that T3 reduces hyperoxia-mediated lung inflammation and injury.

Thyroid hormone has not generally been appreciated as an important regulator of lung function. However, thyroid hormones have a multiplicity of effects on the lung. For example, thyroid hormone increases the number of alveolar type II cells, the number of lamellar bodies, and surfactant release. Systemic or local T3 administration enhances alveolar edema fluid clearance in both normal and hyperoxia-injured rat lungs and hyperoxia-injured rat lungs. Airspace T3 administration rapidly restored the AFC decreased by hyperoxia-induced lung injury in rat lungs. T3 also significantly increases type II alveolar epithelial cell Na,K-ATPase activity, consistent with its role in removing edema fluid from the alveolar space. This action of T3 involves coordinated action of both the PI-3 kinase (PI3K)/Akt and ERK1/2 pathways. The PI-3K/Akt pathway is involved in many cell responses to stress, including inflammation.

Instilled T3 also enhances survival of alveolar Type II cells exposed to hyperoxic stress. Hyperoxic exposure causes both apoptosis and necrosis of alveolar epithelial cells. Survival of alveolar type II (AT2) cells is important for recovery after oxidant-induced lung damage. Thyroid hormone (T3) reduced hyperoxia-induced lung inflammation in adult rats exposed to >95% oxygen in vivo.

Hyperoxia-induced acute lung injury (HALI) in animals is a well-established model of acute lung injury and ARDS. Prolonged exposure to hyperoxia leads to the generation of excessive reactive oxygen species, causing injury and death of alveolar endothelial and epithelial cells accompanied by high alveolar levels of pro-inflammatory cytokines and excessive leukocyte infiltration.

Alveolar epithelial and endothelial cells maintain the integrity of the alveolar-capillary barrier and defend against oxidative injury. Prolonged exposure to hyperoxia generates excessive reactive oxygen species (ROS), damaging cells by overwhelming redox homeostasis. The nuclear factor erythroid 2-related factor 2 (Nrf2) transcription factor protects cells against oxidative insults and chemical carcinogens by coordinated transcriptional activation of a panel of antioxidant/detoxifying enzymes, including heme oxygenase-1 (HO-1), glutathione-S-transferase (GST), NAD(P)H:quinone oxidoreductase-1 (NQO-1), glutamate cysteine ligase, peroxiredoxin 3, peroxiredoxin 6, manganese superoxide dismutase, and catalase. Genetic ablation of Nrf2 enhances lung injury induced by hyperoxia, while amplification of endogenous Nrf2 activity attenuates HALI. Increased expression of antioxidant enzymes and phase 2 detoxifying enzymes in lung epithelial cells protects against the damage caused by hyperoxia-generated ROS. Nrf2-regulated HO-1 confers cytoprotection against cell death in various models of lung injury by inhibiting apoptosis. Nrf2 activation promotes alveolar cell survival during oxidative stress.

Figure 7:
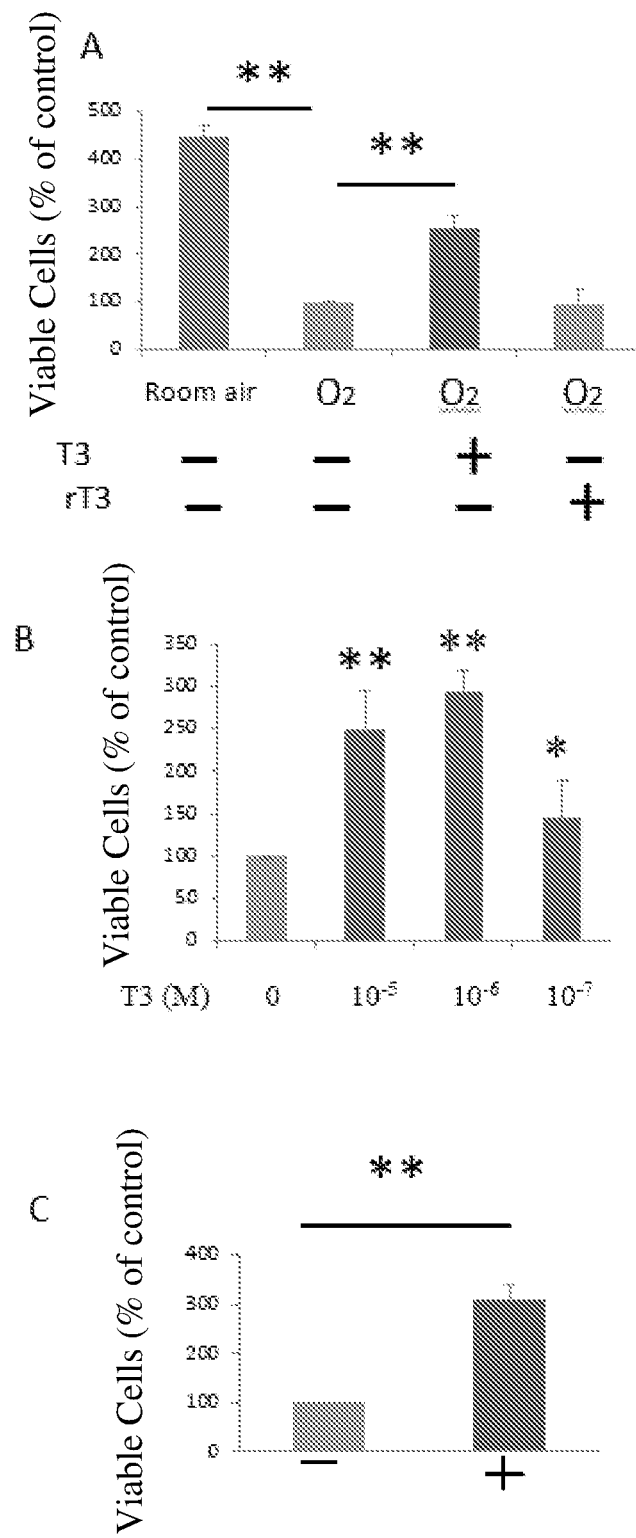
FIG. 7. T3 increases RLE-6TN cell survival under 95% oxygen and during recovery in normoxia. (A) T3 increases RLE-6TN cell survival under hyperoxia stress. The cells were incubated in 90% $O_2$ and 5% $CO_2$ for 72 hours in the present of T3 ($10^{-6}$M for A) or RT3 ($10^{-6}$M for A) in 2% stripped FBS culture medium. (B) T3 Dose curve for RLE-6TN cell survival under hyperoxia. The cells were cultured in DMEM/F12 with 10% FBS in 21% $O_2$ and 5% $CO_2$ overnight. The cells were then incubated in 90% $O_2$ and 5% $CO_2$ for 72 hours in the presence of indicated concentrations of T3 in DMEM/F12 medium supplemented with 2% stripped FBS. (C) RLE-6TN cells were incubated with/without T3 in hyperoxia for 72 hours, and cells were then transferred to room air and cultured in DMEM/F12 with 10% FBS for another 72 hours. The viable cells are counted immediately after 72-hour hyperoxia exposure. Cell viability is assessed with trypan blue. The amount of viable cells under specific conditions is presented as a percentage of the cell number from hyperoxia alone. Data are mean±s.d. of four independent experiments with *=P<0.05; **=P<0.01.

T3 increased the number of viable AT2 cells after 72 hours of exposure to 90% oxygen. In vivo hyperoxia causes rat lung inflammation and injury similar to early phase ARDS and in vitro hyperoxic exposure is a widely used model to study alveolar epithelial cell injury and function in ARDS. Using MDCK cells, cell density determined the balance of apoptosis, necrosis, and cell proliferation during hyperoxia exposure. In vivo hyperoxia exposure dramatically decreases serum T3 while T3 supplementation attenuates hyperoxia-induced lung inflammation. FIG. 7 shows that T3 protects alveolar epithelial cells from hyperoxic damage and increases their survival. Rat adult AT II-like cell line RLE-6TN were exposed to 90% oxygen for 72 hours in the presence or absence of T3 or RT3 (inactive thyroid hormone) and the number of viable cells was measured by trypan blue exclusion. Hyperoxia dramatically decreased the number of surviving AT2 cells by almost 75% compared to room air (21% oxygen) culture conditions (FIG. 7A). T3 significantly increased the number of surviving cells under hyperoxia stress by ~2.5-fold compared with hyperoxia control. In contrast, rT3 had no role in cell survival. The protective effect of T3 was observed across a range of pharmacologic concentrations (10-7 to 10-5 M) (FIG. 7B). When the AT2 cells that had been exposed to hyperoxia for 72 hours with or without exogenous T3 were allowed to recover in room air for an additional 72 hours (with no supplemental T3), the protective effect of T3 on viable AT2 cell number persisted and was of similar magnitude (FIG. 7C). The beneficial effect of having T3 at pharmacologic concentration present during hyperoxia was manifested as more surviving AT2 cells even after a recovery period in room air. These results demonstrated that T3 significantly protected AT2 cell survival during hyperoxia.

Figure 8:
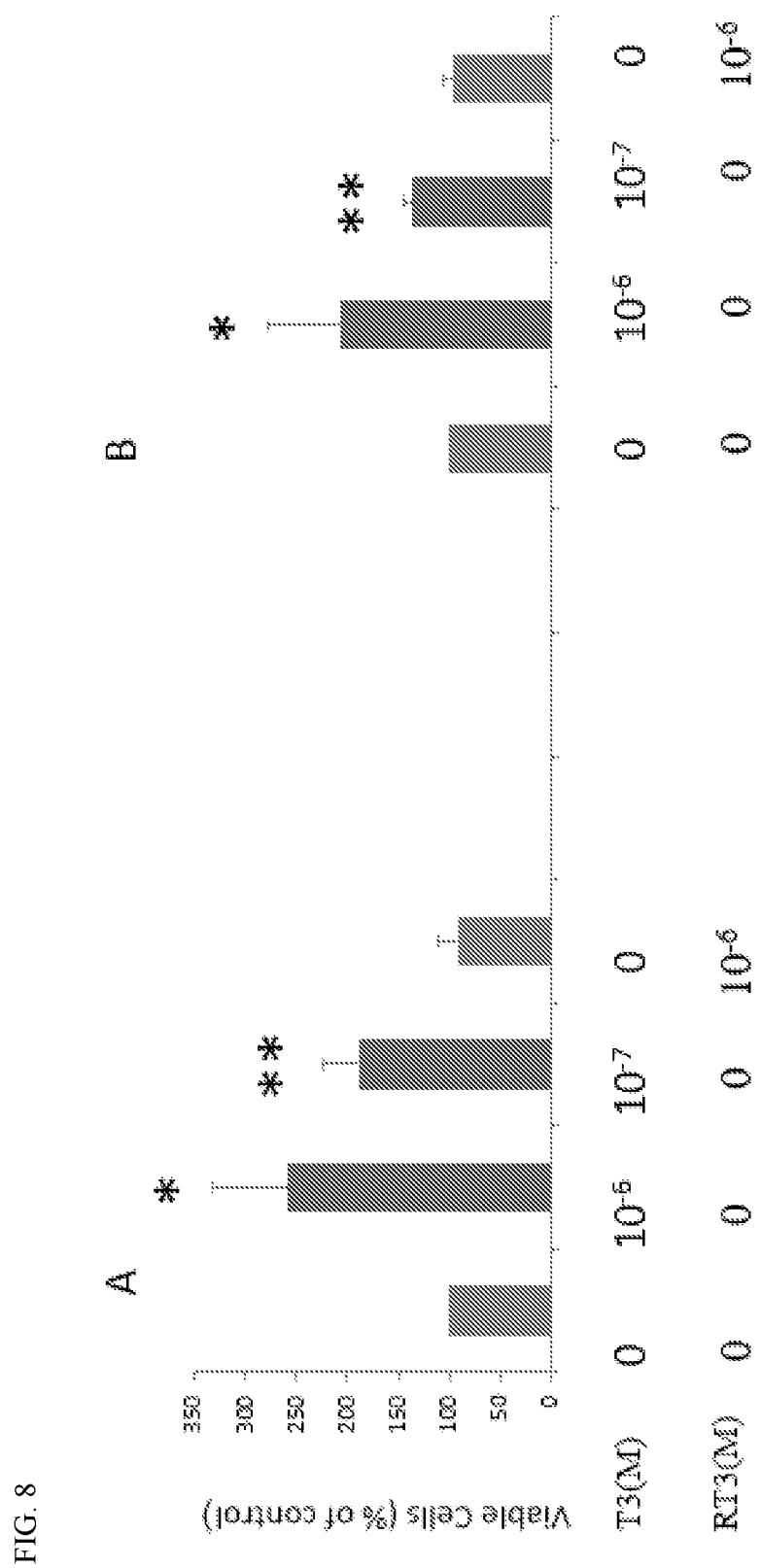
FIG. 8. T3 increases the number of RLE-6TN cells after hyperoxia injury. (A) RLE-6TN cells were exposed to hyperoxia for 24 hours, then were transferred to room air for 48 hours in the presence of T3 or rT3 in DMEM/F12 medium supplemented with 2% stripped FBS. (B) RLE-6TN cells were exposed to hyperoxia for 48 hours, then were transferred to room air for 48 hours in the presence of T3 or rT3 in DMEM/F12 medium supplemented with 2% stripped FBS. In both (A) and (B), the number of viable cells under specific conditions is presented as a percentage of the cell number related to hyperoxia alone in the same experiment. Data are mean±s.d. of four independent experiments with *=P<0.05; **=P<0.01.

T3 augmented recovering AT2 cell number after hyperoxic injury. Alveolar epithelial recovery after lung inflammation and injury promotes the recovery of patients with ARDS. FIG. 8 shows that T3 positively impacted AT2 cell recovery after hyperoxia-induced damage. RLE-6TN cells were exposed to 90% oxygen for 24 hours or 48 hours. Then the cells recovered in 21% $O_2$/5% $CO_2$ in the presence or absence of T3 or rT3 for 48 hours. After either 24 or 48 hours of injury (FIG. 8A and FIG. 8B, respectively) followed by recovery, T3 significantly increased the number of viable AT2 cells at 48 hours of recovery, whereas rT3 had no protective effect. Thus T3 also has a beneficial effect on AT2 cell recovery from hyperoxia if it is present only during the recovery phase.

Figure 9:
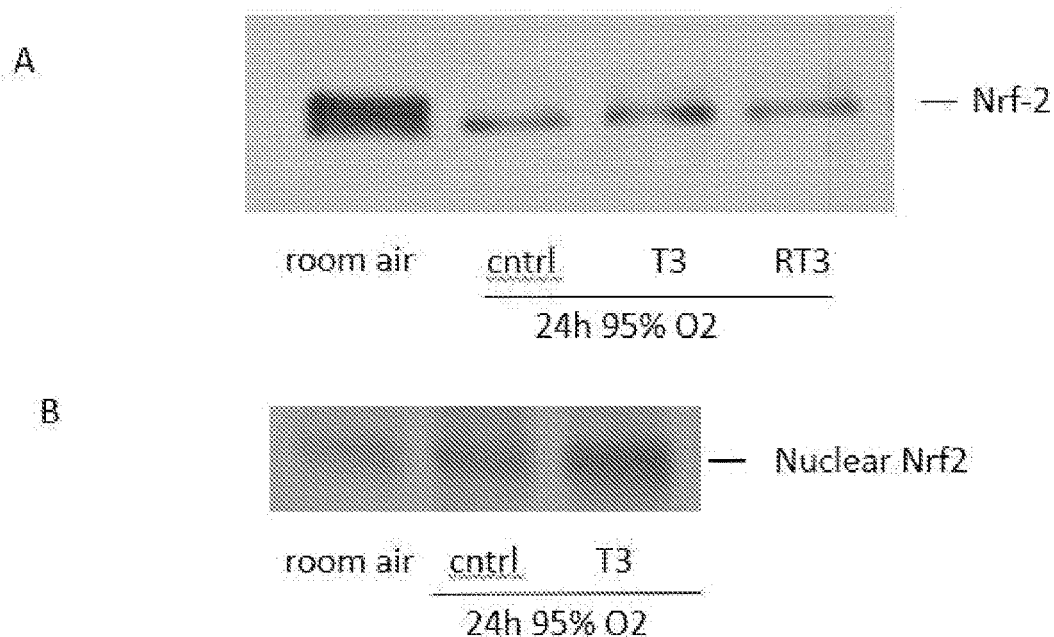
FIG. 9. Protective effect of T3 on hyperoxic damage of ATII requires the Nrf2 activation. RLE-6TN cells were incubated with or without $10^{-6}$ M T3 in 90% $O_2$ and 5% $CO_2$ for 24 hours in the presence of T3 (10-6M) in DMEM/F12 medium supplemented with 2% stripped FBS. The cells were then collected for Western Blotting analysis. (A) Cellular total protein of Nrf2. (B) Nuclear Nrf2.

T3 increased Nrf-2 protein expression and nuclear translocation under hyperoxia stress. The transcription factor Nrf2 (NF-E2-related factor 2) promotes cellular homeostasis, especially during exposure to chemical or oxidative stress. Nrf2 regulates the basal and inducible expression of a multitude of antioxidant proteins, detoxification enzymes, and xenobiotic transporters. FIG. 9 shows that T3 increases Nrf2 activity. Total cellular and nuclear Nrf2 protein were assessed at 24 hours of hyperoxia exposure. Hyperoxia decreased the total Nrf2 protein expression, surprisingly without changing the nuclear Nrf2 protein level. T3 treatment during hyperoxia significantly increased both total cellular and nuclear Nrf-2 protein expression (FIG. 9).

Figure 10:
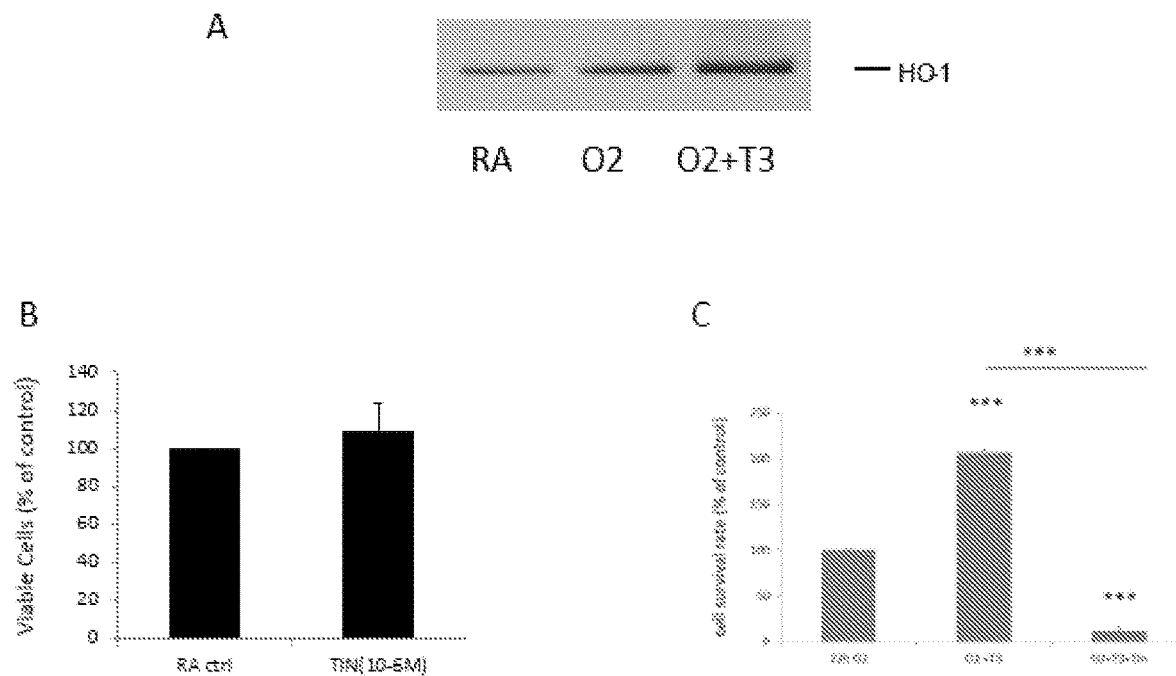
FIG. 10. HO-1 Upregulation is required for T3-increased RLE-6TN cell survival in hyperoxia. (A) T3 increases total cellular HO-1 protein under hyperoxia. The cells were incubated in 90% $O_2$ and 5% $CO_2$ for 72 hours in the present of T3 ($10^{-6}$M). The cells were then collected for Western Blot analysis. (B) The cells were incubated in 21% $O_2$ and 5% $CO_2$ for 72 hours in the present of HO-1 inhibitor Tin Protoporphyrin IX(10-6M) tinT3 ($10^{-6}$M). (C) The cells were incubated in 90% $O_2$ and 5% $CO_2$ for 72 hours in the present of T3 ($10^{-6}$M) or Tin Protoporphyrin (10-6M). Cell viability is assessed with trypan blue. The number of viable cells under specific conditions is presented as a percentage of the cell number related to hyperoxia alone. Data are mean±s.d. of three independent experiments with *=P<0.05; **=P<0.01.

T3-induced increase in HO-1 is required for T3-increased RLE-6TN cell survival in hyperoxia. Heme oxygenase-1 (HO-1) is an anti-inflammatory, antioxidative, and cytoprotective enzyme that is regulated by the activation of the major transcription factor Nrf2. HO-1 is the inducible isoform of the first and rate-limiting enzyme of heme degradation and its induction protects against oxidative stress and apoptotic cell death. Desoxyrhapontigenin upregulates Nrf2-mediated heme oxygenase-1 expression in macrophages and inflammatory lung injury. FIG. 10 shows that T3 altered HO-1 expression in AT2 cells during hyperoxia. RLE-6TN cells were exposed to 90% $O_2$ for 24 hours and then cell survival and HO-1 expression were measured. The impact of the HO-1 inhibitor, tin protoporphyrin, on cell survival also was determined. T3 treatment significantly enhanced total cellular protein of HO-1 during hyperoxia (FIG. 10A). Tin protoporphyrin had no effect on AT2 cell number in room air (FIG. 10B), but it blocked the T3-caused increase in cell survival and augmented cell death (FIG. 10C). Thus, T3 augments HO-1 expression during hyperoxia and HO-1 upregulation facilitates the protective effect of T3 on AT2 cell survival.

Figure 11:
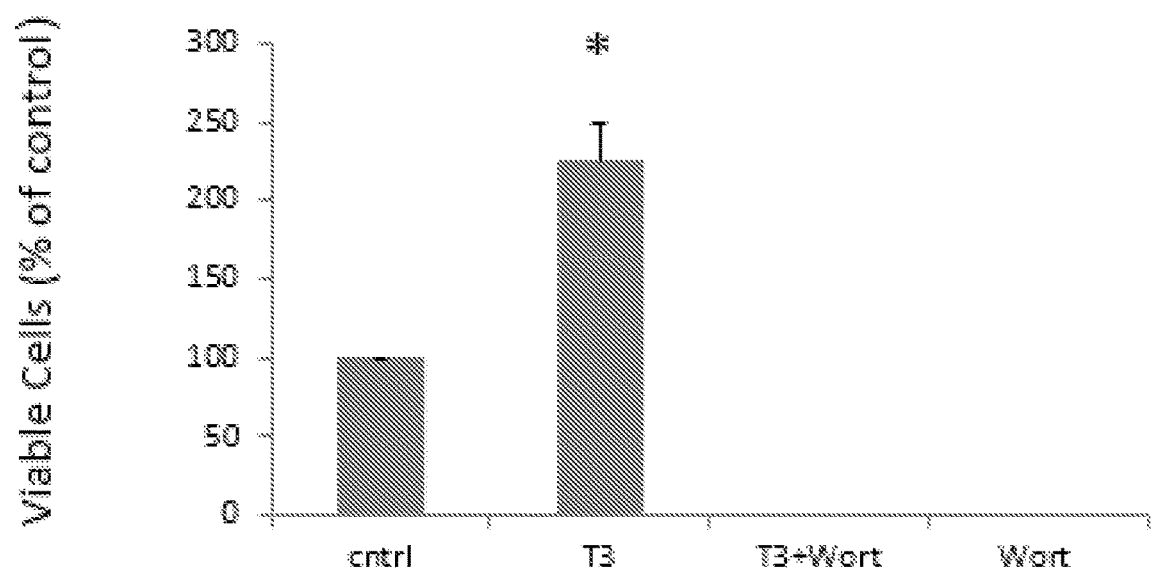
FIG. 11. PI3K inhibitor wortmannin blocked T3-induced cell survival in hyperoxia. The cells were incubated in 90% $O_2$ and 5% $CO_2$ for 72 hours in the present of T3 ($10^{-6}$M) or wortmannin ($10^{-6}$M) in DMEM/F12 medium supplemented with 2% stripped FBS. Cell viability is assessed with trypan blue. The number of viable cells under specific conditions is presented as a percentage of the cell number related to hyperoxia alone. Data are mean±s.d. of four independent experiments with *=P<0.05; **=P<0.01.

PI3-kinase activity medaites the T3 effects on AT2 cell survival, Nrf2 activity, and HO-1 expression. The PI3K/Akt is an anti-apoptotic survival pathway and is regulated by a number of receptor-dependent mechanisms. T3 stimulates PI3K activity and activation of this pathway promotes T3-induced increases of Na,K-ATPase activity and plasma membrane expression. In vascular endothelium, PI3K activation increases HO-1 expression, while PI3K activation augments Nrf2 protein levels and HO-1 activation in other cell types. To detect whether the PI3K/Akt pathway is required for the T3 protective effects on alveolar cell survival, Nrf2 activity and HO-1 protein levels during hyperoxia, RLE-6TN cells were cultured for 72 hours in hyperoxia in the presence of $10^{-6}$M T3 and/or 100 nM wortmannin. Wortmannin blocked the T3-induced cell survival during hyperoxia, and resulted in death of almost all the cells (FIG. 11).

Figure 12:
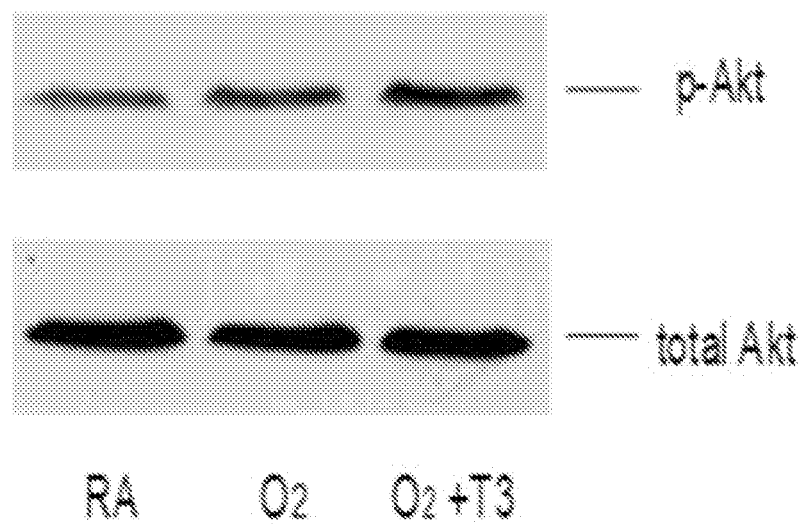
FIG. 12. T3-induced increase in Nrf2 and HO-1 protein via PI3K in hyperoxia. (A) Western Blot and densitometry data for total Nrf2. (B) Western Blot and densitometry data for cytoplasmic Nrf2. (C) Western Blot and densitometry data for nuclear Nrf2.
Figure 12:
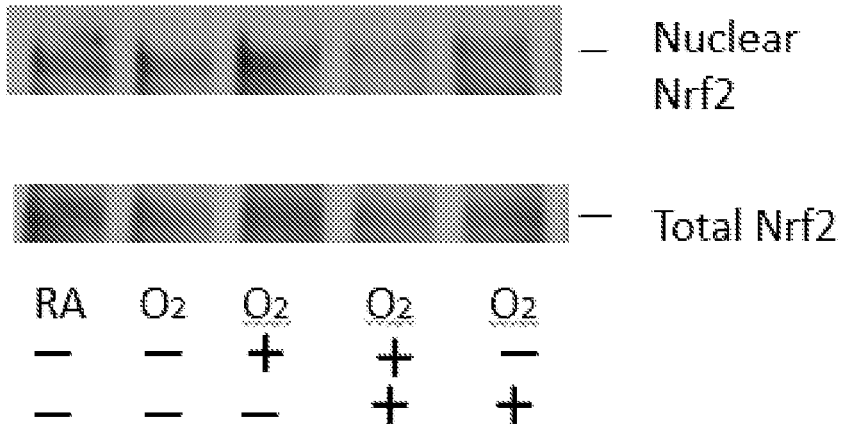
Figure 12:
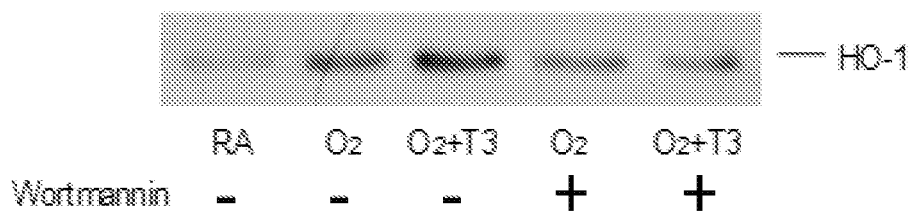

FIG. 12 shows the effect of PI3K on activation of Akt by phosphorylation. The RLE-6TN cells were exposed to hyperoxia for 24 hours and T3 was added for 20 minutes to some cells. Hyperoxia alone did not alter the quantity of total or phospho-Akt compared to room air control cells, whereas T3 augmented phosphorylation of Akt at Ser473 (FIG. 12A) compared with room air control and hyperoxia alone. PI3 kinase is activated by T3 during hyperoxia and activation of this pathway facilitates the protective effect of T3 on AT2 cell survival. In addition, the PI3K inhibitor wortmannin also blocked the T3-induced increases in both Nrf2 total cellular protein and nuclear protein (FIG. 12B), and total cellular amount of HO-1 protein (FIG. 12C). Thus, the PI3-kinase pathway is activated by T3 during hyperoxia and activation of this pathway is involved in the beneficial effects of T3 on the cytoprotective effectors HO-1 and Nrf2 and on AT2 cell survival.

Recovery of the alveolar epithelial barrier is a component of the recovery from ARDS. Protecting alveolar epithelial cells from dying during injury and/or augmenting re-epithelialization are strategies to speed healing. Thyroid hormone has not been conceived as a determinant of lung healing, but serum T3 levels are decreased in both humans and rats with acute lung injury. Lung tissue T3 levels also are markedly decreased. AT2 cells respond to pharmacologic and physiologic concentrations of T3 through both PI3K/Akt and MAP kinase mediated pathways that increase Na,K-ATPase activity and also increases alveolar fluid clearance in vivo.

This disclosure provides data showing that T3 at pharmacologic concentrations increases AT2 cell survival during hyperoxia and accelerated the recovery in AT2 cell number after hyperoxia. These effects were associated with activation of PI3 kinase and Nrf2 and with upregulation of HO-1 expression. The cytoprotective effects of T3 were abrogated when PI3K activation was blocked by wortmannin or when HO-1 expression was blocked by tin protoporphyrin. These findings suggest that T3 augmentation in the lung augments alveolar epithelial repair.

In many studies, exposure of lung epithelial cells to hyperoxia for 60-72 hours causes cell death. However, this disclosure provides data showing that treatment of RLE-6TN cells with T3 prior to exposure to hyperoxia increased viable cell numbers compared to untreated controls. The effect of T3 on cell number may be due, at least in part, to preserving cell proliferation, diminishing cell death by necrosis, diminishing cell death by apoptosis, and/or other mechanisms. T3 augments proliferation in some selected cell types via PI3K pathway activity (human glioma, human pancreatic insuloma), but inhibits proliferation in others (human proximal tubule cell line (HK2) and renal cancer cell lines (Caki-2, Caki-1)). Past studies of cultured AT2 cells have not demonstrated stimulation of proliferation by thyroid hormones. The effect of T3 on cell proliferation appears, therefore, to be cell type specific. The effect of thyroid hormones on cell death across a variety of cell types has not been carefully examined.

Hyperoxic exposure of AT2 cells causes a block in cell proliferation and augments cell death by a combination of necrosis and apoptosis. This disclosure presents data that shows the number of surviving AT2 cells under hyperoxic stress in the presence of T3 was 2.5-fold higher than in hyperoxia alone (FIG. 7), most likely due to a strong cytoprotective role of T3 in hyperoxia. Regeneration and/or restoration of alveolar cells after lung injury improves restoration of normal lung structure and function. T3 also enhanced RLE-6TN cell recovery from hyperoxic injury (FIG. 8).

Nrf-2 is involved in regulating antioxidant defense. Nrf-2 activation in response to oxidant exposure is involved in inducing several antioxidative and cytoprotective enzymes that mitigate cellular stress. In animal studies, Nrf-2 expression is involved in protection against hyperoxic lung injury. Hydrogen gas, a scavenger of reactive oxygen species (ROS), reduces hyperoxic lung injury via Nrf-2 pathway. Lung epithelial and endothelial cell death is main characteristics of hyperoxic lung injury. This disclosure presents data showing that T3 in hyperoxia increases Nrf2 expression and nuclear accumulation (FIG. 9), indicating that T3 increases Nrf2 activity in alveolar epithelial cells. Nrf2 cytosol-to-nuclear translocation may represent a novel cytoprotective mechanism of T3 to limit free radical or electrophile toxicity.

Nrf2, as a sensor for oxidative/electrophilic stress, is constantly degraded through a Keap 1/Cullin3/Ring Box 1 (Cul3/Rbx1) E3 ubiquitin ligase complex pathway in the cytoplasm. When a cell is exposed to oxidative stress, Nrf2 dissociates from the Keap 1 complex, stabilizes and translocates into the nucleus, leading to activation of ARE-mediated gene expression. Several protein kinases including PKC, MAPK/ERK, p38, PERK, and PI3K/Akt can activate Nrf2, while GSK-3beta, whose activity can be inhibited by Akt-mediated phosphorylation at Ser9, inactivates Nrf2. GSK-3beta phosphorylates Fyn, a tyrosine kinase, leading to nuclear localization of Fyn. Fyn phosphorylates tyrosine 568 of Nrf2, resulting in nuclear export of Nrf2, binding with Keap 1, and degradation of Nrf2. 60-minute exposure to hyperoxia increases Nrf2 activity via PI3K/Akt in lung epithelial cells. This disclosure provides data showing that the PI3K inhibitor wortmannin abolished T3-induced increase in nuclear levels of Nrf2 in hyperoxia (FIG. 12B), suggesting that PI3K activation by T3 is involved in Nrf2 nuclear translocation.

Heme oxygenase-1 (HO-1) is an antioxidant enzyme that mediates cytoprotection against oxidative stress. HO-1 prevents hyperoxia-induced lung endothelial death in a mouse model. Up-regulation of Nrf2-mediated heme oxygenase-1 expression by eckol in Chinese hamster lung fibroblast (V79-4) cells via PI3K/Akt pathway. This disclosure presents data demonstrating that T3 increased HO-1 expression in alveolar epithelial cells under in hyperoxic conditions (FIG. 10A). HO-1 inhibitor, TIN, blocked T3-induced increase in cell survival (FIG. 10C). These results indicated that HO-1 facilitates the cytoprotective effect of T3 in hyperoxia.

In summary, upregulation of antioxidative and cytoprotective gene expression by Nrf-2 mediates alveolar epithelial cell survival and/or decreases cell death in response to hyperoxia stress. T3 increases alveolar epithelial cell survival and speeded up cell recovery from hyperoxic injury.

These cytoprotective effects of T3 involve activation of Nrf2 and upregulation of HO-1 gene expression via T3-activated PI3K.

This disclosure therefore describes compositions and methods for maintaining or restoring T3 levels in a subject. Typically, the subject is a human. The compositions generally include T3 in a modified formulation. The modified formula results in a well-tolerated instillant with limited systemic exposure. Instilled T3, in the modified formulation, can be effective for reducing—in some cases, eliminating—lung inflammation (e.g., associated with lung transplant, radiotherapy or chemotherapy), augmenting pulmonary edema fluid clearance, diminishing lung injury, and/or treating lung inflammation associated with pulmonary disease or injury (e.g., ARDS). T3, administered directly into the lungs rather than systemically, is a safe prophylactic and/or therapeutic treatment for lung inflammation.

The conventional T3 liquid formulation is FDA-approved for clinical use to treat myxedema coma/precoma by intravenous administration directly into the bloodstream. The conventional formulation is not pH adjusted because intravenous administration to the bloodstream causes the T3 to be rapidly diluted and buffered by the buffering capacity of serum proteins and other blood components. When the conventional T3 formulation is administered directly into the lung, its concentration is not diluted immediately and the degree of buffering capacity of the lung, both tracheobronchial tree and alveolar-lining fluids is uncertain. Thus, instilling T3 into the airway and lung directly from the manufacturer's vial—i.e., without adjusting the pH—is extremely toxic to rat lung mucosa and airspaces.

The modified formulation described herein includes T3, adjusted to neutral pH (5.5-8.5). The T3 may be formulated with any suitable pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient or is known to be injurious to lung tissue, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with T3 without causing any undesirable biological effects or interacting in a deleterious manner with any of the other components of the pharmaceutical composition in which it is contained.

T3 may therefore be formulated into a pharmaceutical composition. The pharmaceutical composition may be formulated in a variety of forms adapted for delivery to the nasosinus, intratracheal, intrabronchial, or alveolar space. A pharmaceutical composition can be administered to a mucosal surface, such as by administration to, for example, respiratory mucosa (e.g., by spray, aerosol, nebulization, or instillation). A composition also can be administered via a sustained or delayed release. Sustained or delayed released may be accomplished through conventional, general technologies for sustained or delayed drug delivery. Sustained release also may be accomplished by combining the T3 with a second drug that inhibits a mechanism that degrades or clears T3 from the lung. One exemplary second drug is an inhibitor of D3, such as, for example, iopanoic acid.

The modified formulation described herein includes T3, adjusted to neutral pH. As used herein, the term "neutral pH" refers to a pH that is pH 7.0+1.5—i.e., a pH of 5.5 to 8.5. In some embodiments, the formulation may be buffered to a minimum pH of at least 5.5, at least 6.0, at least 6.5, at least 7.0, or at least 7.5. In some embodiments, the formulation may be buffered to a maximum pH of no greater then 8.5, no greater then 8.0, no greater then 7.5, no greater than 7.0, or no greater than 6.5. In some embodiments, the formulation may be buffered to a pH that falls within a range having endpoints defined by any minimum pH listed above and any maximum pH listed above that is greater than the minimum pH. Thus, for example, the formulation may be buffered to a pH of from 5.5-8.5, such as, for example, a pH of 5.5-7.0, a pH of 6.0-8.0, a pH of 6.0-7.0, or a pH of 6.5-7.5.

Thus, T3 may be provided in any suitable form including, but not limited to, a solution, a suspension, an emulsion, a spray, an aerosol, or any form of mixture. The composition may be delivered in formulation with any pharmaceutically acceptable excipient, carrier, or vehicle. Exemplary suitable excipients include, but are not limited to, dextrose and ammonium hydroxide. For example, the formulation may be delivered in a dosage form suitable for direct delivery to the lungs such as, for example, an aerosol formulation, a non-aerosol spray, a solution, a liquid suspension, and the like. The formulation may further include one or more additives including such as, for example, an adjuvant, a colorant, a fragrance, a flavoring, and the like.

A formulation may be conveniently presented in unit dosage form and may be prepared by methods well known in the art of pharmacy. Methods of preparing a composition with a pharmaceutically acceptable carrier include the step of bringing T3 into association with a carrier that constitutes one or more accessory ingredients. In general, a formulation may be prepared by uniformly and/or intimately bringing the active compound into association with a liquid carrier, a finely divided solid carrier, or both.

The amount of T3 administered can vary depending on various factors including, but not limited to, the weight, physical condition, and/or age of the subject; the particular clinical signs or symptoms exhibited by the subject; the type or cause of lung inflammation or pulmonary edema; and/or the method of administration. Thus, the absolute amount of T3 included in a given unit dosage form can vary widely, and depends upon factors such as the species, age, weight and physical condition of the subject, and/or the method of administration. Accordingly, it is not practical to set forth generally the amount that constitutes an amount of T3 effective for all possible applications. The physiologically active T3 concentration at the cellular level has been determined and varies depending upon the cell type and the specific hormonal target effect. Dosing of T3 can be designed to achieve either physiologic or pharmacologic local tissue levels. Those of ordinary skill in the art, however, can determine the appropriate amount with due consideration of such factors.

For example, T3 may be administered to treat pulmonary edema or lung inflammation at the same dose and frequency for which T3 has already received regulatory approval. In other cases, T3 may be administered for treating alveolar edema or lung inflammation at the same dose and frequency at which the drug is being evaluated in clinical or preclinical studies. One can alter the dosages and/or frequency as needed to achieve a desired level of T3. Thus, one can use standard/known dosing regimens and/or customize dosing as needed. However, the primary active form of T3—i.e., the form in which it has the greatest physiological activity—is when the T3 is "free"—e.g., not bound to large proteins such as albumin. Therefore, the physiologic effect of a given amount of T3 also may be influenced by the proteins and other aspects of the environment that it is introduced into. Thus, a smaller amount of T3 may be required to achieve an effective drug delivered dose for the methods described herein—i.e., in the "free" state and delivered directly to the nasosinus, intratracheal, intrabronchial, or alveolar airspace—than the dose of T3 receiving regulatory approval from treating other conditions by intravenous delivery.

In some embodiments, the method can include administering sufficient T3 to provide a deposited dose of, for example, from about 0.5 μg to about 2.0 mg to the subject, although in some embodiments the methods may be performed by administering T3 in a dose outside this range. In some of these embodiments, the method includes administering sufficient T3 to provide a deposited dose of from about 5 μg to about 50 μg to the subject. On a μg/kg basis, the calculated administered T3 dose to achieve physiologic effects could range from as low as 2 ng/kg to 1 mg/kg. As one example, a 50 μg dose can provide a μg/kg dosage range of from about 0.03 μg/kg (to a 160 kg person) to as high as 25 μg/kg (to a 2 kg preterm infant. In many instances, however, dosing on a μg/kg basis is less relevant since direct instillation to lung tissue is not as subject to systemic dilution as, for example, intravenous administration. Lung size in adults does not vary significantly with weight, so mass of T3 delivered is often the more relevant measure of an appropriate dose.

As used herein, the term "deposited dose" or "lung-delivered" dose refers to the amount of T3 deposited to the surface of the respiratory tract. For instillation, the deposited dose is essentially the full dose being instilled. In an aerosol or nebulized formulation, however, the deposited dose is conventionally 10% or less of the drug being aerosolized or nebulized. 90% of the drug is expected to be lost in the delivery apparatus and/or exhaled. This may be greater in the injured ARDS lung. Thus, one may aerosolize or nebulize 500 μg of T3 to achieve an aerosolized or nebulized deposited dose of 50 μg. The use the term "deposited dose" or "lung-delivered" dose normalizes the dose across different routes of administration.

A sufficient deposited dose or lung-delivered dose can provide delivery of a minimum amount of T3 of at least 5 ng such as, for example, at least 100 ng, at least 1 μg, at least 10 μg, at least 50 μg, at least 100 μg, at least 250 μg, at least 500 μg, at least 1 mg, at least 1.5 mg, at least 2 mg, at least 5 mg, at least 10 mg, at least 15 mg, at least 20 mg, or at least 25 mg.

A sufficient deposited dose or lung-delivered dose can provide delivery of a maximum amount of T3 of no more than 50 mg such as, for example, no more than 30 mg, no more than 20 mg, no more than 15 mg, no more than 10 mg, no more than 5 mg, no more than 4 mg, no more than 3 mg, no more than 2 mg, no more than 1.5 mg, no more than 1 mg, no more than 500 μg, no more than 300 μg, no more than 200 μg, no more than 100 μg, no more than 50 μg, no more than 30 μg, no more than 20 μg, or no more than 10 μg.

A sufficient deposited dose or lung-delivered dose also can be characterized by any range that includes, as endpoints, any combination of a minimum deposited dose or lung-delivered dose identified above and any maximum deposited dose or lung-delivered dose identified above that is greater than the minimum deposited dose or lung-delivered dose. For example, in some embodiments, the deposited dose or lung-delivered dose can be from 1 μg to 1.5 mg such as, for example, from 5 μg to 50 μg.

In some embodiments, T3 may be administered, for example, from a single dose to multiple doses per day, although in some embodiments the method can be performed by administering T3 at a frequency outside this range. When multiple doses are used within a certain period, the amount of each dose may be the same or different. For example, a dose of 50 μg in a day may be administered as a single dose of 50 μg, two 25 μg doses, or in multiple unequal doses. Also, when multiple doses are used within a certain period, the interval between doses may be the same or be different. In certain embodiments, T3 may be administered from about once per day, four times per day, or continuously.

In some embodiments, T3 may be administered, for example, from a single dose to a duration of multiple days, although in some embodiments the method can be performed by administering T3 for a period outside this range. In certain embodiments, T3 may be administered once, over a period of three days, or over a period of seven days. In certain embodiments, T3 may be administered from about once per day, four times per day, or continuously. Usually, thyroid hormone replacement for human clinical hypothyroidism is given daily with either thyroxine T4 or combination T4 and T3. A recent study using a single oral dose of 50 micrograms of liothyronine resulted in peak serum concentration at 2.5 hours with a mean half-life of 22.5 hours. There was a lag between the peak serum concentration and the physiologic effect of increased heart rate at five hours. (Jonklaas et al., *Ther Drug Monit.* 37(1): 110-118, 2015). For acute severe human illness with myxedema coma, there is a wide recommended frequency of intravenous T3 administration, from every four hours to every 12-24 hours. Thus, in some embodiments, T3 may be administered once daily by intratracheal instillation at escalating doses with frequent physiologic measurement of hemodynamic parameters and less frequently extravascular lung water (EVLW).

Treating alveolar edema, lung inflammation, or associated conditions can be prophylactic or, alternatively, can be initiated after the subject exhibits the onset of pulmonary edema or lung inflammation or the associated symptoms or clinical signs of a condition. Treatment that is prophylactic—e.g., initiated before a subject experiences an event (e.g., cancer radiotherapy) or manifests a symptom or clinical sign of the condition (e.g., while an infection remains subclinical)—is referred to herein as treatment of a subject that is "at risk" of having the condition. As used herein, the term "at risk" refers to a subject that may or may not actually possess the described risk. Thus, for example, a subject "at risk" of infectious condition is a subject present in an area where other individuals have been identified as having the infectious condition and/or is likely to be exposed to the infectious agent even if the subject has not yet manifested any detectable indication of infection by the microbe and regardless of whether the subject may harbor a subclinical amount of the microbe. As another example, a subject "at risk" of a non-infectious condition is a subject possessing one or more risk factors associated with the condition such as, for example, genetic predisposition, ancestry, age, sex, geographical location, or medical history.

Accordingly, a pharmaceutical composition that includes T3 can be administered before, during, or after the subject first exhibits pulmonary edema, lung inflammation, or other symptom or clinical sign of associated conditions or, in the case of infectious conditions, before, during, or after the subject first comes in contact with the infectious agent. Treatment initiated before the subject first exhibits pulmonary edema or lung inflammation or another associated symptom or clinical sign may result in decreasing the likelihood that the subject experiences clinical consequences compared to a subject to whom the composition is not administered, decreasing the severity and/or completely resolving the lung abnormality. Treatment initiated after the subject first exhibits clinical manifestations may result in decreasing the severity and/or complete resolution of pulmonary edema and/or lung inflammation experienced by the subject compared to a subject to whom the composition is not administered.

For example, hyperoxic injury to rats in vivo and to alveolar type II cells in vitro is decreased when T3 is given in advance of or coincident with injurious hyperoxic exposure. In vitro, alveolar type II cell death was significantly reduced. In vivo, lung inflammation, lung injury, neutrophil infiltration and protein leakage into the alveolar space were significantly reduced.

Thus, the method includes administering an effective amount of the T3 composition to a subject having, or at risk of having, pulmonary edema or lung inflammation. In this aspect, an "effective amount" is an amount effective to reduce, limit progression, ameliorate, or resolve, to any extent, the pulmonary edema or lung inflammation. For example, an "effective amount" of a T3 pharmaceutical composition may increase alveolar fluid clearance, increase the population of alveolar type II pneumocytes, increase the size of alveolar type II pneumocytes, increase Na,K-ATPase activity in alveolar epithelial cells, decrease or repair alveolar damage, decrease hypoxemia, and/or decrease in inflammation throughout the respiratory tract (e.g., nasosinus, intratracheal, intrabronchial and alveolar airspace).

Preliminary studies demonstrate the safety of administering a T3 composition via intratracheal instillation. Safety studies are described in Example 3, below. In a safety study conducted in compliance with Good Laboratory Practices (GLPs), 0.3 mL (300 µl) was administered to rats weighing 250-350 grams via intratracheal instillation daily for five consecutive days. No significant complications or changes were observed with the administration of the materials using a combination of histopathologic, physiologic, and laboratory value assessments. All rats received the same dose of T3 (~2.7 µg in 0.3 mL). The calculated dose of T3 administered based on Day 1 body weight was 10 µg/kg. The calculated dose based on lung weight was about 1.57 µg/g wet lung weight.

Both male and female rats, prior to and throughout dosing, were observed to have slight/mild porphyrin staining. This likely reflects the mild non-specific stress induced by 5 days of handling and transportation with anesthesia and intubation. Since this occurred during the acclimatization and handling period and in the non-T3 treated rats, none of the observations regarding porphyrin staining can be directly attributed to treatment with T3.

On average, body weights for all groups tended to decline within the first two days of dosing. At the time of terminal euthanasia, body weights returned to greater than the pre-dose weights with the exception of the T3 females that weighed slightly less than their pre-dose weight. Prior to terminal euthanasia, male toxicity phase animals weighed between 267.17 g and 309.60 g with a mean±standard deviation of 285.28±11.10 g. Female toxicity phase animals weighed between 240.11 g and 278.44 g with a mean±standard deviation of 258.24±9.79 g.

No clinically significant abnormalities were noted on any animals during daily observations from the time of enrollment on study until euthanasia with the exception of a small number of anesthetic recovery complications noted below that varied in severity and cause. There were no other notable complications throughout the course of the study. All other surviving animals were in apparent good health prior to terminal euthanasia. In the toxicity phase of the study there were four saline control animals and one vehicle control animal that died during recovery from anesthesia post-dosing. These deaths occurred approximately 30-60 minutes post-dosing and were judged by the veterinary pathologist conducting the post-mortem exam to have been caused by exposure to excessive temperatures during recovery from anesthesia on heating pads. There were two T3 test animals that died after dose administration. For one of these deaths, gross pathology findings indicated it to be due to colon impaction, and in the other animal the cause was undetermined but thought to be due to injury during the instillation procedure. Of all animals dosed with the test or control articles, only two of seven early deaths were animals treated with liothyronine sodium injection. In spite of these losses, the dosing of spare animals for each group ensured that the planned number of animals of each sex/group outlined in the study design was achieved.

Hematology and serum chemistry evaluations were performed on all toxicity phase animals that survived to scheduled termination with the exception of one animal that did not receive hematology analysis due to a clotted sample.

Results of the female hematology showed a mildly increased reticulocyte count and degree of polychromasia in the T3 group compared to the control groups (likely clinically insignificant). There were no statistical or clinically significant changes in the hematology parameters in the males. In the chemistry results in the female rats, the only finding was a slight statistical difference in the mean albumin concentration between the T3 group and control groups (likely clinically insignificant). In males, the only difference in the chemistry values was a slight difference in the mean globulin level between the T3 group and control groups. The differences between the T3 and control groups in the mean albumin in females and mean globulins are considered clinically insignificant as the changes were minimal and there are no other clinically significant changes in the laboratory data. The slightly higher reticulocyte count in the T3-treated female rat group likely is not of clinical significance considering the lack of a true reference interval and given the absence of a concurrent decrease in hematocrit, hemoglobin, RBC count, abnormal RBC morphology or evidence of an increase in red blood cell turnover.

In general, the changes noted between the T3 group and control groups are considered clinically insignificant and not directly related to the T3.

The animal necropsy and gross pathology observations were performed by Dr. George Ruth, DVM, PhD, DACVP or Rebecca Rose, DVM, PhD, DACVP. Aside from seven early deaths, all toxicity phase animals were euthanized at the scheduled euthanasia time point. Necropsy was performed on all animals on the day of death with the exception of the five animals that died during recovery from anesthesia, for which necropsy was performed on the day following death. There were no apparent complications during any of the necropsy procedures, and no gross lesions were detected in the lungs of any of the animals in this study. Lesions were detected in a total of four animals from among the three treatment groups on their assigned termination date that probably were associated with terminal intraabdominal injections. No evidence of toxicity was observed grossly, and no clinically significant abnormalities were noted during necropsy that were related to the administration of test or control articles.

Histological evaluation of animals resulted in the following deductions. There were no differences in the organ weight of the lungs related to treatment with T3. All macroscopic findings were consistent with agonal changes, autolysis and or changes related to the intraperitoneal injections and/or intratracheal instillations. All microscopic findings in the lungs were similar in intensity and frequency across treatment groups.

There were seven unscheduled deaths in this study: one vehicle control, four saline controls, and two liothyronine sodium injection animals. In all cases the animals died shortly after intratracheal injection or were found dead post dose. Macroscopic and microscopic findings in all animals were consistent with autolysis and/or agonal change, and the cause of death in the liothyronine sodium injection animals was likely related to the instillation procedure and not test article related. There were no macroscopic or microscopic findings in any of the end organs examined that were determined to be related to treatment with liothyronine sodium injection.

Figure 5:
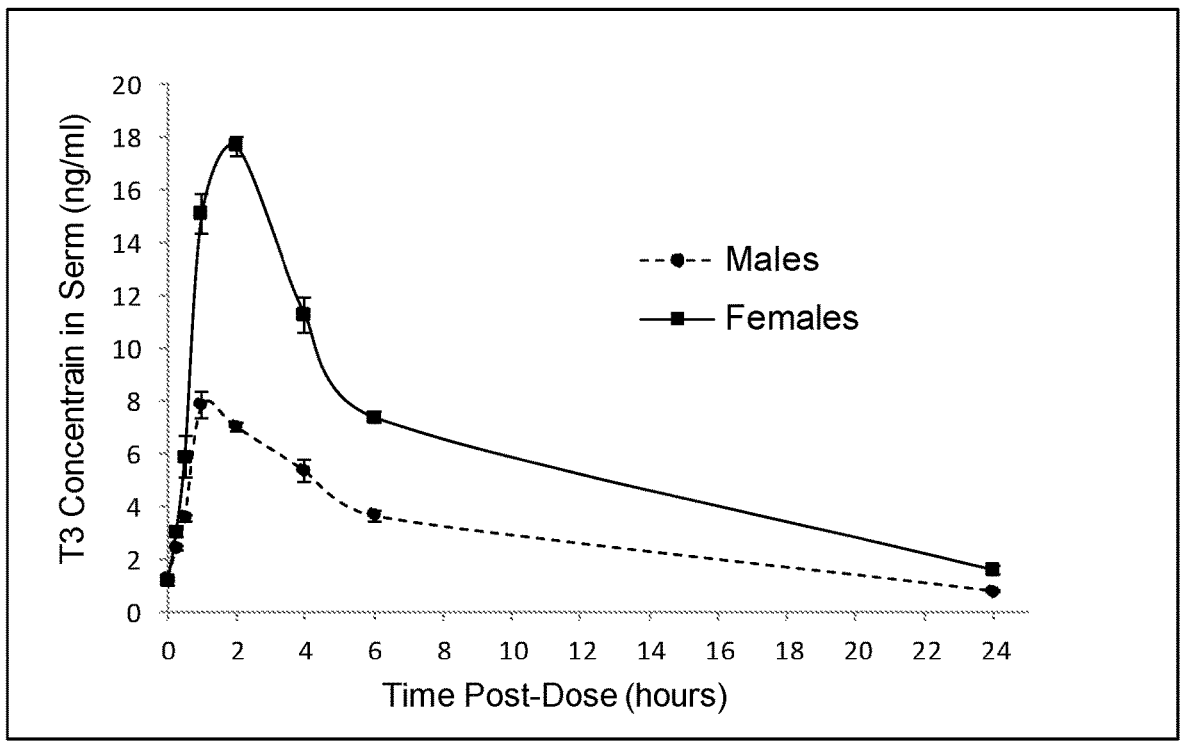
FIG. 5. Time course of change of serum T3 concentration (mean+/−SEM) vs. time in a rat model. A single dose of T3 was administered via intratracheal instillation at a dose of 2.7 (~10.0 μg/kg). Samples were analyzed for total T3 using a chemiluminescence assay. Whenever possible, mean concentrations were derived from three animals/gender/time point.
Figure 6:
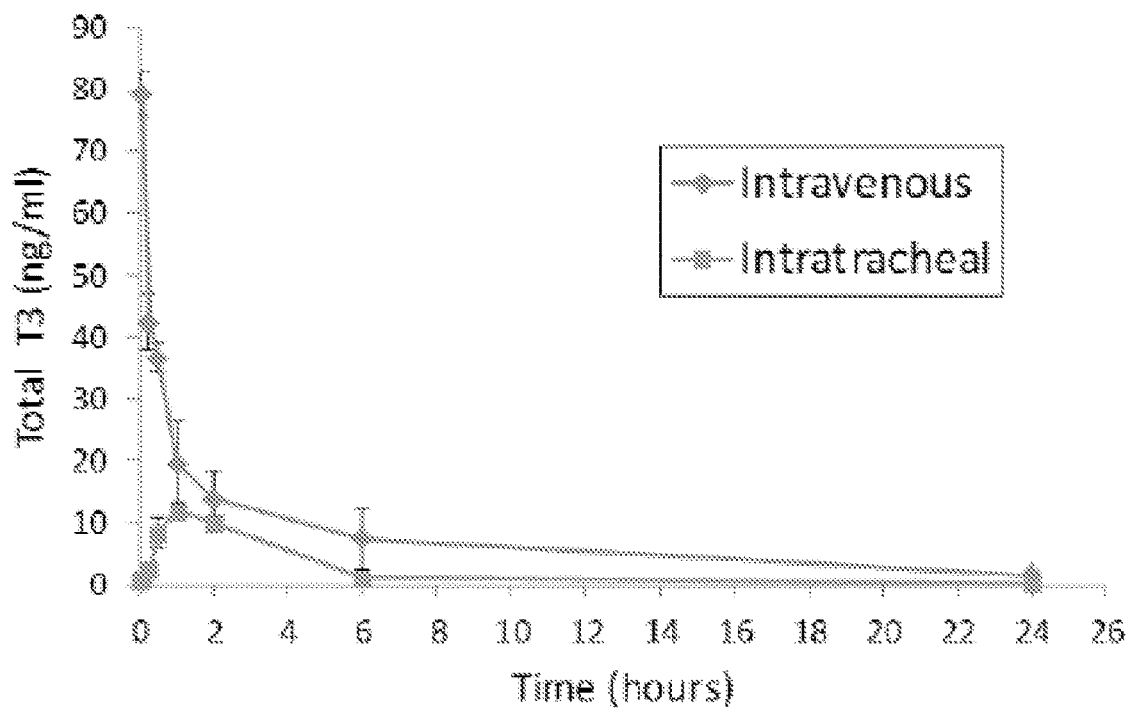
FIG. 6. Serum T3 concentration (mean+/−SEM) following intravenous or intratracheal administration of liothyronine sodium (2.7 μg in 300 μl, pH 7.5) to rats. A single dose of T3 was administered intravenously (diamonds) or via intratracheal instillation (squares). Samples were analyzed for total T3 using a chemiluminescence assay.

T3 was successfully quantified for all of the samples submitted. All reported values were within the limits of quantification for the assay (10 pg/mL-460 pg/mL). The measurable values are shown in FIG. 5 (mean ±standard error). The greater serum T3 concentrations in females versus males is likely due to the somewhat lower body weights for the females, and the finding in preliminary studies that females on average have a larger lung weight/body weight ratio than do males; the relatively larger lung surface area allowing for greater absorption of T3 into the systemic circulation.

Thus, T3 was administered into the lungs by direct instillation with minimal test-material-related adverse events or complications. Seven toxicity phase and zero toxicokinetic phase animals died following dosing procedures.

No adverse T3 related clinical observations were observed during the course of the study. Female rats in the toxicity phase that were administered liothyronine sodium did not regain body weight at the same rate as males or as in control groups. The changes in clinical pathology noted between the T3 group and control groups are considered clinically insignificant and not directly related to the T3.

Peak levels of T3 were observed at the one hour time point for males and the two hour timepoint for females. The values for the males were consistently lower than the corresponding time points in the females. All animals, regardless of body weight, received the same dose of T3. On average, females had lower body weights than males and therefore received a slightly higher calculated dose per body weight and a slightly higher dose per calculated wet lung weight than males.

Administration of the T3, normal saline, or T3 vehicle via intratracheal instillation in a rat model evaluated after five days of administration resulted in no unscheduled deaths that could be attributed to the test or control articles, no differences in the lung weights, and no macroscopic or microscopic findings considered to be related to treatment with T3. Thus, all test materials were successfully dosed with no adverse events or clinically significant test material related complications.

In preliminary, dose-finding studies, there were no acute effects on physiologic parameters (e.g. respiratory rate, $O_2$ saturation, or heart rate) following a single intravenous delivery, or after five days of intratracheal delivery of 3.0 µg neutral pH T3. Also, when 3.0 µg T3 was given intratracheally, the T3 $C_{max}$ was ~$1/17^{th}$ and the AUC ~$1/5^{th}$ of what was seen following intravenous administration of 3.0 µg T3 (data not shown).

The maximum feasible dose used in this study (on a µg of T3 per lung weight basis) is 300-fold higher than the starting dose for a proposed first-in-human clinical trial, providing a significant safety margin.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Human Lung Tissue Procurement

Post-mortem lung tissue was obtained from consecutive adult patients (male and female) with a clinical diagnosis of ARDS. Autopsies were authorized by the Institutional Review Board and performed after family consent, from December 2008 through October 2009. The diagnosis of ARDS was based on the following criteria: $P_aO_2/FIO_2 < 200$ mmHg, wedge <18 mmHg or CVP<12 mmHg, and CXR with bilateral patchy infiltrates as defined by the American European Consensus Conference. ARDS resulted from a variety of etiologies including pneumonia (viral or bacterial), sepsis, trauma and post-surgical lung injury (Table 1). Consecutive adult patients dying of non-pulmonary causes and undergoing autopsy by the Medical Examiner were used as controls (e.g., alcohol overdose, hypothermia, myocardial infarction, and motor vehicle trauma (Table 1).

TABLE 1

| ARDS patients and normal controls | | |
|---|---|---|
| ARDS Patients | ARDS Etiology | Free T3 (pg/mL) |
| 23-year-old male | H1N1 influenza pneumonia | 1.2 |
| 44-year-old male | H1N1 influenza pneumonia | |
| 46-year-old female | MRSA pneumonia/sepsis | |
| 64-year-old male | PCP/CMV pneumonia | |

TABLE 1-continued

ARDS patients and normal controls

| | | |
|---|---|---|
| 80-year-old male | Pneumococcal Pneumonia/sepsis | |
| 40-year-old male | Cholecystitis/sepsis | |
| 63-year-old female | Post-CABG surgery | 1.5 |
| 65-year-old female | Motor vehicle trauma | |

| Normal Controls | Cause of Death | Free T3 (pg/mL) |
|---|---|---|
| 23-year-old male | Alcohol overdose | |
| 63-year-old male | Hypothermia | |
| 54-year-old male | Acute Myocardial infarction | 3.8 |
| 48-year-old female | Motor vehicle trauma | |

MRSA: Methicillin-resistant *Staphylococcus aureus*;
PCP: *Pneumocystis carnii (jiroveci)* pneumonia;
CMV: Cytomegalovirus;
CABG: Coronary artery bypass graft.

The lung samples were procured within four to twelve hours after death. Tissue samples were dissected from the peripheral/sub-pleural parenchyma of the anterior lung fields, sliced into 2-cm×2-cm pieces, flash frozen in liquid nitrogen, and stored at −80° C. for future assays or fixed in formalin and embedded for histological and immunochemical analysis. Staff pathologists (Department of Pathology and Laboratory Medicine, Essentia Health-St. Mary's Medical Center and Duluth Clinic, Duluth, Minn.) assigned a histologic diagnosis to each set of tissue. Lung samples demonstrating diffuse alveolar damage (DAD), including hypercellularity, and hyaline membrane/fibrin deposition, were used as study tissues. Lung samples from patients dying of non-pulmonary causes and demonstrating normal lung histologic architecture were used as control tissues. All samples with equivocal histology were excluded.

Human Lung Deiodinase III (D3) Immunohistochemistry

Immunohistochemistry for detection of D3 was performed using a primary rabbit anti-deiodinase 3 antibody (1:100; gift of Domenico Salvatore, M. D., Ph.D., University of Naples Federico II, Naples, Italy), and a biotinylated goat anti rabbit secondary antibody followed by an avidin biotin complex (Vector Laboratories, Inc., Burlingame, Calif.). Diaminobenzidine (DAB) was used as the chromogen. The following protocol was used: Slides were deparaffinized in xylene and endogenous peroxidase activity was blocked with 0.3% hydrogen peroxide in methanol. The slides were rehydrated and treated with trypsin for 30 minutes at 90° C. After cooling, the sections were blocked with 10% normal goat serum in PBS+0.1% Tween-20 for 30 minutes. The anti-D3 antibody (1:100) was added for one hour at room temperature followed by washing in PBS and incubation with the secondary biotinylated goat anti-rabbit IgG antibody for 60 minutes at room temperature. Avidin Biotin Complex (Vector Laboratories, Inc., Burlingame, Calif.) was incubated with the tissue for 30 minutes followed by development of diaminobenzidine until the desired staining intensity was reached. The slides were counterstained for one minute with hematoxylin, dehydrated and examined. All tissue was identically processed with equal exposure time. Examination and photography was performed using a light microscope (DMRB, Leica Microsystems GmbH, Wetzlar, Germany).

D3 Enzymatic Activity

Frozen lung tissue samples were thawed and sonicated in 0.1 M phosphate and 1 mM EDTA at pH 6.9 with 10 mM dithiothreitol and 0.25 M sucrose. D3 activity was assayed by HPLC using 150 µg of cellular protein, 200,000 cpm of 3, 5,[125I]3′-triiodothyronine (PerkinElmer, Inc., Waltham, Mass.), 1 mM 6N-propylthiouracil (PTU), 10 mM dithiothreitol (DTT), and 0-500 nM unlabeled T3 in each reaction as previously described (Simonides et al., *J Clin Invest* 118:975-983; 2008). Reactions were stopped by adding methanol and the products of deiodination were quantified by HPLC as previously described (Richard et al., *J Clin Endocrinol Metab* 83:2868-2874; 1998). D3 velocities were expressed as fmol of T3 inner-ring deiodinated per mg of sonicate protein per minute (fmol/mg/min). Samples with velocities below the detection limit of the assay were set to the minimum detectable activity (MDA) value, 0.05 fmol/mg/min. The MDA was calculated statistically as three standard deviations above background activity.

Lung Total Tissue T3 Measurement

Thyroid hormones were extracted from human lung samples weighing ~0.5 g using a modification of a previously-described method (Excobare et al., *Endocrinology* 117:1890-1900; 1985). Tissue was homogenized in 4 mL methanol containing 1 mM PTU (methanol-PTU) per gram tissue with a rotor-stator homogenizer at 30,000 rpm for 30 seconds. To assess individual sample percent recoveries, 100 µL of $^{125}$I-T4 tracer (0.02 pg/µL in methanol-PTU) was added to each sample. Chloroform was added at double the volume of methanol-PTU and samples were mixed by vortexing. The mixture was centrifuged at 2000 rpm for 15 minutes and the supernatant liquid was transferred to a clean 50 mL tube. The remaining pellets were subjected to two additional extractions by vortexing in 5 mL chloroform: methanol (2:1) per gram tissue, centrifuging at 2000 rpm for 15 minutes, and removing and combining the supernatant with the first extract. To the combined extracts, 1 mL 0.05% $CaCl_2$ was added for every 5 mL of extract. The mixture was vortexed and centrifuged at 2000 rpm for five minutes. The upper aqueous layer, containing thyroid hormones, was transferred to a clean 50-mL tube. The lower organic layer was re-extracted two more times with a volume of pure upper layer (chloroform:methanol:0.05% $CaCl_2$, 3:49:48) equal to the amount of upper layer removed in the previous step. The combined extracted upper layers were subjected to rotary evaporation to remove the remaining chloroform and methanol. The aqueous mixture was shell-frozen and evaporated to complete dryness by lyophilization. Each lyophilized sample was dissolved in 500 µL stripped rat serum and T3 levels were measured using a serum total T3 RIA assay kit (Siemens Medical Solutions Diagnostics; Los Angeles, Calif.), as previously described (Bastian et al., *Endocrinology* 151:4055-4065; 2010).

Statistical Analysis

Statistical analysis of D3 activities and tissue T3 levels was performed using one-way analysis of variance and Tukey's post hoc multiple comparison test. Statistical analyses and data graphing were carried out using the Prism (GraphPad Software, La Jolla, Calif.) software package. Data are presented as mean±SEM. An $\alpha=0.05$ was chosen to define significant differences.

Example 2

Study Design: First In-Human Clinical Trial as Described in FDA-Approved Investigative New Drug (#126204).

Informed consent is obtained within 24-hours prior to administering the study drug. For both the Treatment Group (Intervention) and Control Group (Non-Intervention), the study protocol will be started at Time 0 with a 6-hour EVLWI/PVPI measurement, a 12-hour EVLWI/PVPI measurement, a 24-hour EVLWI/PVPI measurement, a 48-hour EVLWI/PVPI measurement, a 72-hour EVLWI/PVPI measurement, and a 96-hour EVLWI/PVPI measurement.

Study Drug

Human ARDS patients are treated with liothyronine sodium (T3), which is a synthetic form of thyroid hormone T3. Liothyronine sodium is provided in amber-glass vials containing 10 (10 mcg/ml in 1 ml vials) of liothyronine sodium in a sterile non-pyrogenic aqueous solution of 6.8% alcohol (by volume), 0.175 mg anhydrous citric acid, and 2.19 mg ammonium hydroxide. Prior to instillation, the liothyronine sodium is adjusted to neutral pH (6-8) by adding 1.0 N HCL prior to diluting in 0.9% normal saline (NS) under sterile conditions by an appropriately trained pharmacist.

Liothyronine sodium is formulated for administration as follows: 5 µg dose (0.5 ml liothyronine sodium+0.9% NS to 10 ml total volume); 10 µg dose (1.0 ml liothyronine sodium+0.9% NS to 10 ml total volume); 25 µg dose (2.5 ml liothyronine sodium+0.9% NS to 10 ml total volume); 50 µg dose (5.0 ml liothyronine sodium+0.9% NS to 10 ml total volume).

Treatment Group (Intervention)

50 patients receive treatment. Upon enrollment and measurement of baseline values, patients receive 5 µg T3 by airway instillation. Patients are monitored for 24 hours for adverse effects and changes in EVLWI. After 24 hours, if no adverse effects are seen and EVLWI and/or PVPI is unchanged, patients receive a 2× escalated dose of 10 µg T3 by airway instillation. Patients are monitored for 24 hours for adverse effects and changes in EVLWI. and/or PVPI. At t=48 hours from first T3 dose, if no adverse effects are seen and EVLWI is unchanged, patients receive a 2.5× escalated dose of 25 µg T3 by airway instillation. Patients are monitored for 24 hours for adverse effects and changes in EVLWI and/or PVPI. At t=72 hours from first T3 dose, if no adverse effects are seen and EVLWI is unchanged, patients receive a 2× escalated dose of 50 µg T3 by airway instillation. A final EVLWI and PVPI measurement is made 24-hours after final T3 dose at time=96 hours (end time point).

Control Group (Non-Intervention)

The control group includes 18 patients. Upon enrollment and measurement of baseline values, control patients receive no research intervention. Control subjects receive standard of care. EVLWI and PVPI are measured at Time 0 (before treatment), at six hours, 12 hours, 24 hours, 48 hours, 72 hours, and 96 hours.

Primary Study Endpoints

Prior to commencing the study protocol and continuously thereafter, safety and tolerability of the airway to instilled T3 therapy are assessed. Subjects will be monitored for composite endpoints, including pulmonary events (e.g., progressive hemoptysis; quantity ≥30 ml blood-stained sputum), cardiac events (e.g., new sustained ventricular arrhythmia (duration >30 seconds); new sustained accelerated junctional arrhythmia (rate >80 bpm) with worsened hypotension; new sustained atrial fibrillation with rapid ventricular response (ventricular rate >160 bpm) with worsened hypotension; or cardiac arrest (asystole or pulseless electrical activity); and/or hypertensive crisis (systolic >200, or diastolic >120, or change in MAP >20 mmHg).

Secondary Study Endpoints

To assess the efficacy of airway-instilled T3 on reducing EVLWI and/or PVPI in ARDS patients, EVLWI, PVPI, and oxygenation (arterial blood gas, ABG) are measured on subjects in both the Treatment Group and the Control Group beginning at baseline (T=0) and at six hours, 12 hours, 24 hours, 48 hours, 72 hours, and 96 hours thereafter. Additional serial measurements include blood pressure (BP), mean arterial pressure (MAP), central venous pressure (CVP), cardiac index (CI), systemic vascular resistance index (SVRI), oxygen saturation $O_{2sat}$. Finally, serum free T3, free T4, and TSH are measured at each time interval.

Example 3

Test System

This study was conducted using both male and female Sprague-Dawley rats (Envigo, Huntingdon, United Kingdom). Evaluation of the safety of the tracheal route of instillation for liothyronine sodium injection in human clinical trials can be accomplished in this species at appropriate dose levels. Furthermore, responses to thyroid hormone in rats are similar to responses in humans, and the choice of the rat model is based in large part on pharmacologic data from studies of thyroid hormone and associated receptors and physiological responses in rat lung. The University of Minnesota is accredited by the Association for the Assessment and Accreditation of Laboratory Animal Care, International (AAALAC) and registered with the United States Department of Agriculture to conduct research in laboratory animals. Animal studies conformed to NIH guidelines (Guide for the Care and Use of Laboratory Animals. NIH publication No. 86-23. Revised 1985). The protocol was reviewed and approved, as applicable, by the Institutional Animal Care and Use Committee (IACUC) at the University of Minnesota for compliance with regulations prior to study initiation or implementation of amended activities.

Summary of Toxicology Study Design

Details of the study design are shown in Table 1. Sixty animals (plus two spare animals/sex/group) were anesthetized and dosed via intratracheal instillation of test or control materials for five consecutive days. On the day after the last dose a terminal blood collection was performed for clinical pathology, after which animals were euthanized and a gross examination of all organs was performed by a board certified veterinary pathologist. Select tissues were collected for histopathology. Twenty-four animals in the toxicokinetic (TK) phase were anesthetized and dosed with a single intratracheal instillation of T3. Terminal blood collection was performed at two designated time points per animal up to 24 hours after administration for toxicokinetic evaluation. TK animals were euthanized without further evaluation after the final blood collection. All animals were acclimated for a minimum of seven days prior to the dosing procedure. Animals underwent baseline observations and examinations prior to the initiation of the study, and clinical observations and body weight monitoring were performed throughout the in-life portion of the study. All animals received the same dose volume (0.3 mL) of either test or control materials. This maximum feasible dose (MFD) is constrained by the maximum volume that can be safely and reproducibly (over five days) instilled into lungs of rats weighing 250 g to 350 g, which was determined in preliminary toxicology studies to be 0.3 mL. Actual doses delivered are reported as both µg/kg body weight and µg/gm wet lung weight. The toxicity phase animals were 72-135 days of age at the time of initial dosing. Males weighed between 256.52 g and 307.50 g with a mean±standard deviation of 286.74±11.77 g, and females weighed between 250.46 g and 299.01 g with a mean±standard deviation of 260.64±10.34 g. The TK phase animals were 68-144 days of age at the time of initial dosing. Males weighed between 261.23 g and 316.19 g; females weighed between 250.06 g and 280.32 g.

TABLE 1

Study Design

| Group | Toxicity Phase Number of Toxicity Animals | | Toxicokinetic (TK) Phase Number of TK Animals | | Dose Volume |
|---|---|---|---|---|---|
| | M | F | M | F | |
| 1 T3 Vehicle (Control) | 10 + 2[a] | 10 + 2[a] | 0 | 0 | 300 μL |
| 2 Normal Saline (Control) | 10 + 2[a] | 10 + 4[a] | 0 | 0 | |
| 3 T3 (Test Article) | 10 + 2[a] | 10 + 2[a] | 12 + 2[b] | 12 + 2[b] | |
| Totals | 30 + 6 | 30 + 8 | 12 + 2 | 12 + 2 | |
| | 60 + 14 | | 24 + 4 | | |
| Dosing Frequency & Duration | *Once daily for 5 days | | Single Dose | | |
| Scheduled Termination | 1 day post final dose | | Day 1 | | |
| TK Blood Collection | NA | | At designated time points | | |
| Histology | Yes | | NA | | |

F = Females,
M = Males,
NA = Not Applicable

[a] Use of Spares-Two spare animals of each sex/toxicity group were dosed with the animals from each group so that they were available for replacement within the similar timeframe. An additional two females were dosed in Group 2 due to early deaths experienced due to non-test material-related issues. The spare animals underwent terminal clinical pathology and gross necropsy evaluations.
[b] Use of Spares-Four (4) additional unused spares were released from study at the direction of the Study Director.

Test and Control Materials

T3 used for this study was liothyronine sodium injection (X-GEN Pharmaceuticals, Inc., Horseheads, N.Y.) supplied in 1.0 mL amber glass vials at a concentration of 10 μg in 1.0 mL. Each mL of liothyronine sodium injection contains, in sterile, non-pyrogenic USP grade water, liothyronine sodium equivalent to 10 μg of liothyronine (T3), 6.8% alcohol by volume, 0.175 mg anhydrous citric acid and 2.19 mg ammonia (as ammonium hydroxide). In preliminary studies it was determined that rats do not tolerate intratracheal instillation of liothyronine sodium at a pH of >10.0 as it is supplied commercially. Therefore, the liothyronine sodium and the vehicle were adjusted to neutral pH (6.0-8.0) with sterile 1.0 N HCl (Sigma-Aldrich, St. Louis, Mo.) added aseptically in a biosafety cabinet prior to intratracheal instillation into animals. Using aseptic technique, vials of liothyronine sodium were opened and the entire contents were transferred into sterile 1.5 mL Eppendorf tubes. 80-90 μL of 1.0 N HCl was added to the tube and gently vortexed, and the pH was measured using pH test strips (pH 4.5 to 10.0, Ricca Chemical Co., Arlington, Tex.). Additional HCl was titrated in gradually, as needed, until the pH was in the desired range. There is a volume increase of approximately 10% after adjusting the pH to neutral with 1.0 N HCl, resulting in a final concentration of liothyronine sodium of approximately 2.73 μg T3/300 μL (9.17 μg/ml). This solution was stored at 4° C. and used for up to 26 hours after pH adjustment procedure. The vehicle control solution was prepared in sterile, non-pyrogenic USP grade water (USP/EP Purified, Ricca Chemical Co., Arlington, Tex.) and contained, per mL of solution, 6.8% ethanol (Decon Laboratories, Inc., King of Prussia, Pa.) by volume, 0.175 mg anhydrous citric acid (Sigma-Aldrich, St. Louis, Mo.) and 2.19 mg ammonia (J. T. Baker Chemical Co., Avantor Performance Materials LLC, Radnor, Pa.), ammonia solution, strong 27.0-30.0%, N. F.-F. C. C.). The vehicle was also adjusted to neutral pH (6.0-8.0) with 1.0 N HCl as described above. Using aseptic technique the vehicle was filter sterilized and aliquoted into 21 sterile disposable tubes (5 mL each) and stored at 4° C., and a new tube was opened for each day of use. Normal Saline (0.9% Sodium Chloride Injection USP, B. Braun Medical, Inc., Bethlehem, Pa.), was stored at room temperature. A new package was opened for each day of use.

In-Life Animal Care

Upon arrival animals were visually examined by trained staff and weighed, counted, sexed, and appropriately separated into housing boxes. Each animal received a metal ear tag containing an individual identifier prior to initial dosing. Animals were housed in AAALAC accredited pens under sanitary conditions and were socially housed to provide enrichment and companionship. The temperature and humidity of the housing area was monitored a minimum of once daily. Animals were acclimated for a minimum of seven days prior to dosing initiation. Preconditioning was allowed during this period to acclimate the animals to the handling they would experience during weighing, examinations and dosing procedures. All animals were given food (TEKLAD, Envigo, Huntingdon, United Kingdom) and potable tap water ad libitum. Animals were not fasted for procedures. Veterinary care was available throughout the course of the study. Observations on general health, including animal activity, appearance, food and water intake, mortality/moribundity and other endpoints (Table 2) were performed and recorded at least once daily from the time of enrollment on study until euthanasia by a trained technician. A Veterinarian was notified of abnormalities in activity or appearance. To prevent bias with regard to observations, health concerns or treatments, veterinary and general animal care personnel were not informed of dose group distribution.

TABLE 2

In-life Observations/Assessments & Health Monitoring

| Activity | Frequency |
|---|---|
| Handling & Restraint Pre-Conditioning | SID beginning within 2 days after arrival |
| Body Weight (grams) | Within 1 days prior to and/or on the day of initial dose. |
| | Minimally 2-3 times/week during dosing |
| | Day of term |
| Cage Side Observations Mortality/Alive or Dead | Minimally SID beginning within 3 days prior to initial dose. |
| Defecation | Day of term |
| Urination | |
| Behavior/vocalization | |
| Posture/Attitude/Activity | |
| Food available | |
| Water available, bottle intact | |
| Bedding sufficient | |
| Detailed Clinical Observations | At least once prior to initial dosing |
| Posture/Attitude | At least once after initial dose |
| Integument/Hair | Day of Term |
| Eyes | |
| Ears | |
| Nose | |
| Respiratory | |
| Musculoskeletal | |
| Urogenital | |
| Gastrointestinal | |
| Neurological | |

Dosing Procedure

Test and control materials were drawn into dosing syringes using aseptic technique. Using a 18G needle, 0.5 mL of air was drawn into a 1 cc syringe followed by 0.3 mL (300 µL) of the solutions. Animals were anesthetized with a combination of ketamine, 40 mg/kg to 200 mg/kg, and xylazine, 1 mg/kg to 7 mg/kg intraperitoneally (IP), to effect. The dose was adjusted daily, as needed, based on individual animal response and recovery. Depth of anesthesia was evaluated by toe pinch, and eye lubricant was applied to the eyes. An upright, inclined stand was used to support the animals in the desired position during the dosing procedure by suspending the animals from a soft, non-latex rubber band at the top of the stand by their front incisors. Up to 20 µL of 2% lidocaine was applied topically to the back of the throat using a blunt gavage needle prior to intubation with a tracheal catheter to minimize laryngeal spasms and facilitate tracheal placement. The animals were removed from the stand and positioned in prone position while the lidocaine took effect.

After allowing adequate time for lidocaine to take effect, the animals were again suspended on the apparatus, and a catheter (INTRAMEDIC 1.19 mm inner diameter, 1.70 mm outer diameter, Thermo Fisher Scientific, Waltham, Mass.) was inserted into the trachea by first visualizing the larynx through the oral cavity with the aid of an external light source directed at the throat. Holding the tongue aside with blunt forceps and gauze moistened with water helped with visualization of the airway. The catheter was advanced into the trachea to a pre-determined depth approximately 1.0 cm short of the branch point of the major bronchi (measured on a cadaver animal with the trachea and bronchi exposed). Catheter placement in the airway was verified by the fogging of a dental mirror placed at the opening of the catheter. The needle on the dosing syringe was then inserted into the catheter, and the test material and bolus of air was rapidly delivered in a one-to-two second interval. The air bolus administered after the test material facilitated administration of the fluid into the lower airways and ensured that fluid was not retained in the trachea or major bronchi, as confirmed in preliminary experiments using a dye solution. The tracheal catheter was removed from the airway and the animal gently removed from the support apparatus. The animal was placed in a prone position on a heating pad with the chest elevated for a minimum of two minutes after instillation. After two minutes, the animal was placed flat on a heating pad until fully recovered.

Terminal Euthanasia Procedures
Blood Collection for Clinical Pathology (Hematology and Clinical Chemistry)

Blood samples from the toxicity phase animals for clinical pathology were collected one day after the final (fifth) intratracheal dose. Animals were anesthetized with isoflurane 2-5% and oxygen 1-1.5 L/min by inhalation anesthesia via nose cone as needed. For hematology, ≥0.5 mL whole blood was collected via the orbital sinus through plain or coated microhematocrit capillary tubes into $K_2$EDTA collection tubes (BD Biosciences, Thermo Fisher Scientific, Waltham, Mass.) containing an additional 30 µL of 2% EDTA solution (Sigma-Aldrich, St. Louis, Mo.), and kept at 4° C. until same day analysis. For serum chemistry, ≥0.75 mL whole blood was collected via the orbital sinus through uncoated capillary tubes into red top serum microtubes (Sarstedt AG & Co. K G, Nümbrecht, Germany). For serum collection, tubes were maintained at room temperature for 30 to 60 minutes after collection and then centrifuged at 10,000×g for five minutes at 4° C. The resultant serum was separated and stored at ≤−70° C. if analysis was to occur the following day or kept at 4° C. for same day analysis. All samples were sent to the University of Minnesota-Veterinary Medical Center (VMC) clinical pathology laboratory for analysis. Parameters evaluated for hematology are provided in Table 3. Parameters evaluated for clinical chemistry are provided in Table 4. Following blood collections animals were euthanized with EUTHASOL (Virbac Corp., Fort Worth, Tex.) ≥86 mg/kg IP to effect prior to necropsy. Assessment of the clinical pathology values was performed by Jill Schappa Faustich, DVM, DACVP, University of Minnesota.

TABLE 3

| Hematology |
| --- |
| Red Blood Cell Count (RBC) |
| Hemoglobin Concentration (HGB) |
| Free Plasma HGB |
| Hematocrit (HCT) |
| Mean Corpuscular Volume (MCV) |
| Mean Corpuscular Hemoglobin (MCH) |
| Mean Corpuscular Hemoglobin Concentration (MCHC) |
| Reticulocyte Count (Retic Absolute And Relative) |
| Platelet Count (Plt & PCT Absolute And Relative) |
| Mean Platelet Volume (MPV) |
| Platelet Distribution Width (PDW) |
| Red Cell Distribution Width (RDW) |
| White Blood Cell Count (WBC) |
| Neutrophil Seg Count (NEUT Absolute And Relative) |
| Neutrophil Band Count (BAND Absolute And Relative) |
| Lymphocyte Count (LYMPH Absolute And Relative) |
| Monocyte Count (MONO Absolute And Relative) |
| Eosinophil Count (EOS Absolute And Relative) |
| Basophil Count (BASO Absolute And Relative) |
| Mast Cells (Absolute And Relative) |
| Unclassified Cell Count (Absolute And Relative) |

TABLE 4

| Serum Chemistry |
| --- |
| Blood Urea Nitrogen (BUN) |
| Creatinine (Creat) |
| Calcium (Ca) |
| Phosphorous (Phos) |
| Magnesium (Mg) |
| Protein (TP) |
| Albumin (Alb) |
| Globulin (Glob) |
| Alb/Glob ratio$^a$ |
| Sodium (Na) |
| Chloride (Cl) |
| Potassium (K) |
| Bicarbonate (HCO3) |
| Osmolality (Osmol) |
| Anion Gap (An Gap) |
| Bilirubin, Total (T.Bili) |
| Alkaline Phosphatase (ALP) |
| Gamma-Glutamyl Transferase(GGT) |
| Alanine Transferase (ALT) |
| Aspartate Transferase (AST) |
| Creatine Kinase (CK) |
| Glucose (Gluc) |
| Cholesterol (Chol) |
| Amylase |
| Lipemia Icterus Hemolysis (LIH) |

Toxicokinetics (TK)
Blood Collection

For toxicokinetic experiments, rats were anesthetized with combination of ketamine 40 mg/kg to 200 mg/kg and xylazine 1 mg/kg to 7 mg/kg, intraperitoneally (IP), to effect for dosing procedures, and dosed intratracheally with liothyronine sodium injection as previously described. The details of the TK sample collection protocol are provided in Table 5 and Table 6. Depending on the duration of time between dosing and the first or second blood collection time points, animals either had blood collected while still anesthetized under the injectable anesthetics, or if recovered, they were anesthetized with Isoflurane 2-5% and oxygen 1-1.5 L/minute by inhalation anesthesia via nose cone, as needed, to maintain adequate anesthesia depth (assessed by toe pinch). Topical proparicaine anesthetic ophthalmic solution was applied to each eye prior to performing the first blood collection and allowed time to take effect. Collection of serum samples for TK analysis was as described for serum chemistry samples above, and samples were stored at ≤−70° C. until assayed. Animals were euthanized with EUTHASOL (Virbac Corp., Fort Worth, Tex.) ≥86 mg/kg IP to effect following the final blood collection.

TABLE 5

Toxicokinetic Blood Collections

| TK Group | Total Number of Males/Females | Sample Collection Time Points Number of animals M/F per Occasion (Target Time Post Dose) Two time points per animal | | | | | | | |
|---|---|---|---|---|---|---|---|---|---|
| | | T0 | 15 min | 30 min | 1 hr | 2 hr | 4 hr | 6 hr | 24 hr |
| Test Article | 12/12 | 3/3 | 3/3 | 3/3 | 3/3 | 3/3 | 3/3 | 3/3 | 3/3 |

TABLE 6

Toxicokinetic Animal Distribution per Timepoint

| | T0 | 15 min | 30 min | 1 hr | 2 hr | 4 hr | 6 hr | 24 hr |
|---|---|---|---|---|---|---|---|---|
| Male | X | | X | | | | | |
| Male | | X | | X | | | | |
| Male | | | X | | | | X | |
| Male | | | | | X | X | | |
| Female | X | | | | X | | | |
| Female | | X | X | | | | | |
| Female | | | | X | | | X | |
| Female | | | | | | X | X | |

Three animals of each sex/timepoint

Three Animals of Each Sex/Timepoint

Bioanalytical Procedure

For assessment of serum $T_3$ levels samples were sent to the Fairview University of Minnesota Medical Center East Bank Diagnostic Laboratory for analysis, a clinical laboratory certified by CLIA and CAP. Prior to sending serum samples to the analytical lab each sample was diluted 1:4 or 1:8 in normal (0.9%) saline. These dilutions, determined in preliminary studies, ensured that sample total T3 concentrations would fall within assay range (10 pg/mL to 460 pg/mL). Samples were analyzed by a chemiluminescence assay for total triiodothyronine (T3).

TK Analysis

An evaluation of the TK analysis was performed by Dick Brundage, PhD, University of Minnesota. Toxicokinetic parameters were estimated using Phoenix 64 WinNonlin pharmacokinetic software version 7.0. (Pharsight Corp., Mountain View, Calif.). A non-compartmental (NCA) approach consistent with the route of administration was used for parameter estimation. All parameters (Table 7) were generated from mean T3 concentrations in serum from all timepoints unless otherwise stated. Whenever possible, mean concentrations were derived from three animals/gender/time point. Parameters were estimated using sampling times relative to the start of each dose administration. The raw data was converted to ng/ml of serum by dividing the pg/dl values by 100 and then multiplying by the dilution factor for that sample, either 4 or 8. Values below the limit of quantification were calculated as 0.

TABLE 7

TK Parameters Estimated

| Parameter | Description of parameter |
|---|---|
| $C_{max}$ | The maximum observed arithmetic mean concentration of $T_3$ measured after dosing. |
| $C_{max}/D$ | The $C_{max}$ divided by the dose administered. |
| $T_{max}$ | The time after dosing at which the maximum observed arithmetic mean concentration of $T_3$ was observed. |

TABLE 7-continued

TK Parameters Estimated

| Parameter | Description of parameter |
|---|---|
| $AUC_{(0-t)}$ | The area under the $T_3$ arithmetic mean concentration versus time curve from time zero the time after dosing at which the last quantifiable concentration of the drug was observed estimated by the linear or linear/log trapezoidal method. |
| $AUC_{(0-t)}/D$ | The $AUC_{(0-t)}$ divided by the dose administered. |

When data permitted, the slope of the terminal elimination phase of each arithmetic mean concentration versus time curve was determined by log-linear regression, and the following additional parameters were estimated:

Additional Parameters Estimated

| Parameter | Description of parameter |
|---|---|
| $T½$ | The apparent terminal elimination half-life. |
| $AUC_{(0-inf)}$ | The area under the arithmetic mean concentration versus time curve from time zero to infinity. |
| $AUC_{(0-inf)}/D$ | $AUC_{(0-inf)}$ divided by the dose administered. |
| CL | Clearance: the apparent volume of plasma cleared of $T_3$ per unit time following intravenous dosing. |
| $V_d$ | The apparent volume of distribution of $T_3$, determined from the terminal elimination phase following intravenous dosing. |

Calculation of arithmetic means and standard deviations for the matrix concentration data was performed/replicated in EXCEL (Microsoft, Corp., Redmond, Wash.) for reporting purposes. In addition to parameter estimates from mean concentration vs. time curves, the standard error of the $AUC_{(0-t)}$ and $C_{max}$ by dose group, day, and gender (as appropriate) were generated using WINNONLIN (Cetara USA, Inc., Princeton, N.J.).

$C_{max}$ and $T_{max}$ were obtained by inspection of the data. Since measurable endogenous compound is present based on the observed concentration at time zero, a baseline subtraction was performed. Using the mean concentration data, the concentration at time zero was subtracted from the remaining concentrations for male and female animals. The area-under-the-curve (AUC) of the baseline subtracted concentrations was calculated using the linear trapezoidal rule. Since the 24-hour concentration in both male and female animals had approximately returned to the baseline (pre-dose) concentration, these observations were ignored in calculations for the AUC and half-life. The terminal elimination half-life was calculated from the last three observations at 2 hours, 4 hours, and 6 hours. WinNonlin NCA performs linear regression on the logs of the concentrations. The Uniform weighting scheme was selected. The default regression algorithm for NCA will not use $C_{max}$ in the calculation of half-life, even if it appears to be part of the log-linear profile, nor will it provide any half-life based on only two observations. The default regression for the male animals was used. However, for the female animals, the concentration at time two hours was also the $C_{max}$ value. Since it appeared to fall on the regression line of all three concentrations (adjusted R squared=1.0), it was included in the calculation of the half-life. Parameters were evaluated as appropriate at the discretion of the evaluator. Results are provided as individual values, and include graphing of mean and standard error using EXCEL (Microsoft, Corp., Redmond, Wash.) and WINNONLIN (Cetara USA, Inc., Princeton, N.J.) per appropriate groups when possible.

Necropsy Procedures

Gross Pathology

Toxicity Phase animals that were euthanized at scheduled termination or that were found dead or euthanized prior to scheduled termination, were subjected to an extensive necropsy performed by a board certified veterinary pathologist. The necropsy included an examination of the animal carcass and musculoskeletal system, external surfaces and all of its orifices, and cervical, thoracic, abdominal and pelvic regions, cavities and contents. Eyes were not examined due to terminal orbital blood collection methods.

Histopathology

The primary target tissues assessed in this study for histopathalogic changes included the lungs, the tracheabronchi branch point and the tracheobronchial lymph nodes. The intact heart-lung pluck including all target tissues noted above was removed from the animal intact. The heart-lung pluck was weighed, photographed and the lungs were then perfusion inflated via the trachea with 10% neutral buffered formalin (NBF). For inflation, an 18 g butterfly catheter connected to a reservoir of 10% NBF was inserted into the trachea and the lungs inflated for two minutes at a constant pressure of ~20-25 cm, after which the trachea was tied off with suture to maintain inflation of the lungs during fixation. The entire heart lung pluck was then immersion fixed in 10% NBF. Prior to further processing for histology, the heart, trachea and any other adherent tissues were removed from the lungs and weighed. This weight, when subtracted from the weight of the heart-lung pluck taken at necropsy, provided the wet lung weight used in subsequent calculations of actual dose delivered. Non-target tissues including the brain, heart, liver, spleen, pancreas, kidneys and adrenal glands were evaluated for gross lesions. The non-target organs were collected whole with the exception of the liver, in which a representative specimen was collected from the anterior right lobe, and were stored in 10% NBF for potential future analysis. Histological processing and evaluations were performed by Dr. Joan Wicks, DVM, PhD, DACVP, Alizée Pathology, LLC, Thurmont, Md.

Dose Administration

All doses were administered via intratracheal instillation at the maximum volume that could be safely and reproducibly delivered daily for five consecutive days, determined in preliminary studies to be 0.3 mL (300 μl) for rats weighing 250-350 grams. There were no apparent complications with the administration of the materials with the exception of one instance of 20-50 μl of vehicle control article coming out of the top of the dosing syringe during Dose 3 administration to LRT 633 (T3 vehicle group).

The calculated dose of T3 administered based on body weight on the initial day of administration (Day 1) and based on calculated wet lung weights are detailed in Table 8.

TABLE 8

Calculated T3 Dose. Toxicity Phase

| Calculated Dose | | Group 3 All | Group 3 Males | Group 3 Females |
|---|---|---|---|---|
| μg T3/g Wet Lung Weight | Average (SD) | 1.57 (0.61) | 1.50 (0.15) | 1.63 (0.14) |
| μg T3/kg Body Weight | Average (SD) | 10.00 (0.64) | 9.45 (0.33) | 10.55 (0.25) |

1.0 ml T3 (10 μg/ml) diluted with ~100 μl 1.0N HCl to pH, 10 μg in 1.10 ml = 2.73 μg in 300 μl dose Toxicokinetics (TK)

Liothyronine sodium (T3) was successfully quantified for all of the samples submitted. All reported values were within the limits of quantification for the assay (10 pg/mL-460 pg/mL).

The measurable values are listed in Table 9 and are graphed in FIG. 5 (mean±standard error). TK analysis was performed on diluted samples from all 24 animals that received a single T3 dose (Table 10).

TABLE 9

T3 Detected in Serum in Single Dose TK Study
$T_3$ (ng/mL) Means and Standard Errors of Mean (SEM)

| | 0 | 15 min | 30 min | 1 hr | 2 hr | 4 hr | 6 hr | 24 hr |
|---|---|---|---|---|---|---|---|---|
| Male | 1.16 | 2.24 | 3.48 | 8.44 | 6.72 | 6.08 | 3.96 | 0.76 |
| | 1.28 | 2.52 | 3.76 | 6.84 | 6.92 | 4.52 | 3.24 | 0.80 |
| | 1.20 | 2.44 | 3.36 | 8.16 | 7.28 | 5.36 | 3.64 | 0.72 |
| Mean | 1.21 | 2.40 | 3.53 | 7.81 | 6.97 | 5.32 | 3.61 | 0.76 |
| SEM | 0.04 | 0.08 | 0.12 | 0.49 | 0.16 | 0.45 | 0.21 | 0.02 |
| Female | 1.44 | 2.56 | 4.92 | 15.60 | 17.68 | 12.32 | 7.52 | 1.84 |
| | 0.88 | 3.20 | 5.16 | 16.08 | 18.32 | 11.48 | 6.92 | 1.24 |
| | 1.04 | 3.24 | 7.44 | 13.68 | 16.96 | 10.00 | 7.64 | 1.60 |
| Mean | 1.12 | 3.00 | 5.84 | 15.12 | 17.65 | 11.27 | 7.36 | 1.56 |
| SEM | 0.17 | 0.22 | 0.80 | 0.73 | 0.39 | 0.68 | 0.22 | 0.17 |

TABLE 10

Noncompartmental analysis of TK samples

| Sex | Cmax (ng/mL) | Cmax_D (ng/mL/ug) | Tmax (hr) | HL_Lambda_z (hr) | AUClast (hr*ng/mL) |
|---|---|---|---|---|---|
| F | 16.53 | 6.12 | 2.00 | 2.85 | 64.08 |
| M | 6.60 | 2.44 | 1.00 | 3.17 | 25.38 |

| Sex | AUCINF_obs (hr*ng/mL) | AUCINF_D_obs (hr*ng/mL/ug) | Cl_F_obs (mL/hr) | Vz_F_obs (mL) |
|---|---|---|---|---|
| F | 89.70 | 33.22 | 30.10 | 123.60 |
| M | 36.34 | 13.46 | 74.29 | 339.44 |

Example 4

Cell Culture and Hyperoxia Exposure

The adult rat AT2 cell line RLE-6TN (ATCC, Manassa, Va.) was cultured in DMEM/F12 medium with 10% FBS and in a 95% air, 5% $CO_2$ environment until they reached ~50% confluence, then the cells were exposed to 95% $O_2$, 5% $CO_2$ in the presence or absence of T3 in DMEM/F12 with 2% stripped FBS for specified time periods. At the end of the hyperoxia exposure period, the viable cells were counted by trypan blue dye exclusion.

Nuclear Extraction

Nuclei were extracted with NE-PER nuclear and cytoplasmic extraction reagents kit (Thermo Fisher Scientific, Inc., Waltham, Mass.) following the manufacturer's instruction.

Cell Lysis and Western Blot

The cells were lysed in lysis buffer containing 20 mM Tris·HCl (pH 7.5), 150 mM NaCl, 1 mM EDTA, 1 mM EGTA, 1% (vol/vol) Triton X-100 with protease inhibitors (1 mM PMSF, 2 μg/ml pepstatin, and 10 μg/ml each of aprotinin and leupeptin), and phosphatase inhibitors (2.5 mM sodium pyrophosphate, 1 mM β-glycerophosphate, and 1 mM $Na_3VO_4$). The lysate was drawn 10 times through a 25-gauge needle on ice for further lysis and then was centrifuged at 13,000 rpm for 15 minutes at 4° C. The supernatant was collected, and the protein concentrations were determined by use of the BCA protein assay kit (Sigma-Aldrich, St. Louis, Mo.). Immediately after this step, equal amounts of protein were subjected to Western blotting analysis.

Nuclear Extraction

Nuclei were extracted with NE-PER nuclear and cytoplasmic extraction reagents kit (Thermo Fisher Scientific, Inc., Waltham, Mass.) following the manufacturer's instruction.

Statistics

All data are expressed as means±SD of a minimum of three or more independent experiments, unless otherwise noted. In most experiments, individual data points within an experiment represent the mean of at least two replicates. Comparisons involving three or more groups were analyzed by ANOVA and post hoc pairwise comparisons. Differences between means were considered significant at $P<0.05$.

Example 5

Experimental Design

All experimental protocols for animal treatments were approved by the University of Minnesota Institutional Animal Care and Use Committee. Specific pathogen-free (SPF) adult male Sprague Dawley rats (250 g-300 g) receiving intraperitoneal (ip) injections of either saline or T3 were exposed to normobaric hyperoxia ($FI_{O2}>95\%$, 5 LPM) in a chamber with ad libitum access to food and water at room temperature for 48 or 60 hours to induce lung inflammation and injury. The room-air control rats were kept in the University animal housing facility. Rats were injected intraperitoneally with T3 or saline at doses and time points detailed in two protocols summarized in Table 11. At the end of hyperoxic exposure, rats were sacrificed by intraperitoneal pentobarbital injection, and the lungs were harvested; the right lobes were allocated for histopathology, measurement of lung tissue myeloperoxidase (MPO) activity and wet-to-dry weight ratio. The left lobes underwent bronchoalveolar lavage (BAL) to determine BAL protein concentrations and differential cell counts.

TABLE 11

| Experimental protocols | | | | | | |
|---|---|---|---|---|---|---|
| | 0 hours | 12 hours | 24 hours | 36 hours | 48 hours | 60 hours |
| Protocol 1 | | | | | | |
| Control (saline) | ip | ip | ip | ip | ip | end |
| T3 (12.5 μg/kg) | ip | ip | ip | ip | ip | end |
| Protocol 2 | | | | | | |
| Control (saline) | ip | | ip | | end | |
| T3 (15.0 μg/kg) | ip | | ip | | end | |

Wet-Dry Lung Weight Ratios

A portion of the right lung was rinsed briefly in PBS, blotted, and then weighed to obtain the "wet" weight. Lungs then were dried in an oven at 80° C. for seven days to obtain the "dry" weight.

Lung Lavage Analyses

Bronchoalveolar lavage (BAL) of the left lung was performed using a modification of a method previously described (Pace et al., Exp Lung Res 35:380-398, 2009). Briefly, 4 mls of ice-chilled 1× PBS (pH 7.4) were instilled into the left lung, withdrawn, and re-instilled two subsequent times prior to analysis of the lavage fluid. The retrieved BAL fluid was centrifuged at 1500 rpm for 10 minutes to remove cells and debris. The cell pellet was resuspended in 1 ml of 1× PBS (pH 7.4) and total cell number was counted using a hemocytometer. BAL cytospin preparations were stained using the Hema3 stain kit (Thermo Fisher Scientific, Inc., Waltham, Mass.) to identify the nucleated cells. The protein concentration was determined on the supernatants of BAL fluid using a standard BCA assay (Sigma-Aldrich, St. Louis, Mo.).

Myeloperoxidase (MPO) Assay

To quantify the neutrophil activity in the lung, MPO activity was assayed as previously described (Abraham et al., J Immunol 165:2950-2954, 2000). Lung tissues without prior lavage were frozen in liquid nitrogen, weighed, and stored at −86° C. The lungs were homogenized for 30 seconds in 1.5 ml 20 mM potassium phosphate, pH 7.4, and centrifuged at 4° C. for 30 minutes at 40,000×g. The pellet was resuspended in 1.5 ml 50 mM potassium phosphate, pH 6.0, containing 0.5% hexadecyltrimethylammonium bromide, sonicated for 90 seconds, incubated at 60° C. for two hours, and centrifuged at 14,000 rpm for 30 minutes at 4° C. The supernatant was assayed for peroxidase activity corrected to lung weight. MPO was expressed as activity per gram of lung tissue.

Histochemistry

Lung tissue was removed and inflation fixed at 20 cm water pressure in 4% paraformaldehyde, paraffin embedded, cut as 5 micron sections and mounted onto poly-L-lysine slides. Sections were deparaffinized in xylene, rehydrated through a graded alcohol series in methanol, and placed in a 98° C. water bath for 30 minutes in citrate buffer (pH 6.0) for antigen retrieval. After quenching with 0.3% hydrogen peroxide in PBS, sections were incubated in normal serum for 30 minutes and for 15 minutes each with Avidin/Biotin Blocking Kit (Vector Laboratories, Inc., Burlingame, Calif.). After overnight incubation with Myeloperoxidase Ab-1 (Thermo Fisher Scientific, Inc., Fremont, Calif.) at 4° C., Biotinylated goat anti-rabbit IgG (1:500) and RTU Streptavidin (Vector Laboratories, Inc., Burlingame, Calif.) were applied sequentially for 30 minutes and 3,3'-diaminobenzidine was used as a peroxidase substrate. Sections were counterstained with hematoxylin. Image analysis and photography used a Leica Leitz DMRB microscope.

Serum T3 Measurements

Blood samples were collected at the end of 60 hours of hyperoxia and were centrifuged at 13,000 rpm for 30 minutes at 4° C. Supernatant was stored at −20° C. Serum total T3 concentrations were measured with commercial RIA kits (Siemens Medical Solutions Diagnostics, Los Angeles, Calif.) as previously described (Bastian et al., *Endocrinology* 151:4055-4065, 2010).

Statistical Analysis

Values were expressed as means±SD of a minimum of three experiments. Comparisons involving three or more groups were analyzed by ANOVA and post hoc pairwise comparisons. Differences between means were considered significant at p<0.05, adjusted for the number of comparisons.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A pharmaceutical composition for administering directly to the lung of a subject, the composition comprising:
   a salt of triiodothyronine in an amount effective to provide a lung-delivered dose of from 100 ng to 2 mg; and
   a pharmaceutically acceptable buffer; wherein the composition delivered to the lung has a pH from 5.5 to 8.5 and a maximum volume of no more than 0.30 ml per 1.67 g wet lung weight per dose.

2. The pharmaceutical composition of claim 1, wherein the composition is aerosolized.

3. The pharmaceutical composition of claim 1, wherein the composition is nebulized.

4. A method for treating a subject having, or at risk of having inflammation of lung tissues, the method comprising:
   administering to the subject an amount of the composition of claim 1 effective to ameliorate lung inflammation, wherein the composition is administered directly to the pulmonary tract.

5. The method of claim 4, wherein the composition is administered by intratracheal instillation.

6. The method of claim 4, wherein the composition is administered by inhalation of an aerosolized formulation.

7. The method of claim 4, wherein the composition is administered by inhalation of a nebulized formulation.

8. The method of claim 4, wherein the composition is administered prior to the subject manifesting any symptom or clinical sign of lung inflammation.

9. The method of claim 4, wherein the composition is administered after the subject manifests a symptom or clinical sign of lung inflammation.

10. The method of claim 4, wherein the lung inflammation is a clinical sign of acute respiratory distress syndrome (ARDS).

11. The method of claim 4, wherein the lung inflammation is a symptom or clinical sign of premature birth, chest trauma, congestive heart failure, lung transplant, lung cancer radiotherapy, lung cancer chemotherapy, smoking, exposure to a pollutant, hypersensitivity pneumonitis, a reactive/obstructive lung disease, aspiration chemical pneumonitis/pneumonia, pneumonia, an infection of the nasosinus, intratracheal, intrabronchial or alveolar airspace, a connective tissue disease, Wegener's granulomatosis, Good pasture disease, acute eosinophilic pneumonia, chronic eosinophilic pneumonia, medication-related lung injury, cryptogenic organizing pneumonia, Churg-Strauss syndrome, congenital lung disease, or structural lung disease.

12. A method for treating a subject having, or at risk of having lung injury, the method comprising:
   administering to the subject an amount of the composition of claim 1 effective to ameliorate a symptom or clinical sign of lung injury, wherein the composition is administered directly to the pulmonary tract.

13. The method of claim 12, wherein the composition is administered by intratracheal instillation.

14. The method of claim 12, wherein the composition is administered by inhalation of an aerosolized formulation.

15. The method of claim 12, wherein the composition is administered by inhalation of a nebulized formulation.

16. The method of claim 12, wherein the composition is administered prior to the subject manifesting any symptom or clinical sign of lung injury.

17. The method of claim 12, wherein the composition is administered after the subject manifests a symptom or clinical sign of lung injury.

18. The method of claim 12, wherein the lung injury is a clinical sign of acute respiratory distress syndrome (ARDS).

19. The method of claim 12, wherein the lung injury is a symptom or clinical sign of premature birth, chest trauma, congestive heart failure, lung transplant, lung cancer radiotherapy, lung cancer chemotherapy, smoking, exposure to a pollutant, hypersensitivity pneumonitis, a reactive/obstructive lung disease, aspiration chemical pneumonitis/pneumonia, pneumonia, an infection of the nasosinus, intratracheal, intrabronchial or alveolar airspace, a connective tissue disease, Wegener's granulomatosis, Good pasture disease, acute eosinophilic pneumonia, chronic eosinophilic pneumonia, medication-related lung injury, cryptogenic organizing pneumonia, Churg-Strauss syndrome, congenital lung disease, or structural lung disease.

* * * * *